(12) United States Patent
Dong et al.

(10) Patent No.: US 12,419,519 B2
(45) Date of Patent: Sep. 23, 2025

(54) MEDICAL DEVICE

(71) Applicant: Shenzhen Mindray Bio-Medical Electronics Co., Ltd., Shenzhen (CN)

(72) Inventors: Shenhui Dong, Shenzhen (CN); Xuegang Zhang, Shenzhen (CN); Chao Zhu, Shenzhen (CN); Jian Cen, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 658 days.

(21) Appl. No.: 17/876,297

(22) Filed: Jul. 28, 2022

(65) Prior Publication Data

US 2023/0010925 A1    Jan. 12, 2023

Related U.S. Application Data

(63) Continuation of application No. 16/283,573, filed on Feb. 22, 2019, now Pat. No. 11,510,578, which is a
(Continued)

(51) Int. Cl.
*G06F 1/16* (2006.01)
*A61B 5/00* (2006.01)
(Continued)

(52) U.S. Cl.
CPC .............. *A61B 5/00* (2013.01); *A61B 5/021* (2013.01); *A61B 5/02141* (2013.01);
(Continued)

(58) Field of Classification Search
CPC .......... H05K 5/15; H05K 5/10; H05K 5/0217; H05K 5/0247; H05K 5/0256; H05K 5/03;
(Continued)

(56) References Cited

U.S. PATENT DOCUMENTS

| 4,715,385 | A | | 12/1987 | Cudahy et al. |
| 4,895,161 | A | * | 1/1990 | Cudahy ................. A61B 5/339 |
| | | | | D24/186 |

(Continued)

FOREIGN PATENT DOCUMENTS

| CN | 101163378 A | 4/2008 |
| CN | 201727499 U | 2/2011 |

(Continued)

OTHER PUBLICATIONS

United States Patent and Trademark Office, U.S. Appl. No. 16/283,573, Notice of Allowance dated Sep. 29, 2022, 10 pages.
(Continued)

*Primary Examiner* — Anthony M Haughton
(74) *Attorney, Agent, or Firm* — PV IP PC; Wei Te Chung

(57) ABSTRACT

A medical device, comprising a housing, a combined modular structure which is formed by connecting a board card and an interface panel to a main bracket; a first opening arranged on the housing for the insertion of the combined modular structure; a first locking structure for locking and fixing the combined modular structure to the housing; a screen assembly; a second opening arranged on the housing for mounting the screen assembly, and a second locking structure for locking and fixing the screen assembly to the housing. The integral arrangement of a functional module of a medical device helps to improve the assembly precision between various components, and ensure the reliability of the connection between components. The housing adopts an integral structure, has good waterproof and dustproof effects as well as low production costs; the present disclosure facilitates the assembly of board card and other components, as well as module configuration and modular testing while also having good seismic performance.

20 Claims, 17 Drawing Sheets

Related U.S. Application Data continuation of application No. PCT/CN2017/098692, filed on Aug. 23, 2017.

(51) Int. Cl.

| | |
|---|---|
| *A61B 5/021* | (2006.01) |
| *H05K 5/00* | (2025.01) |
| *H05K 5/15* | (2025.01) |
| *H05K 7/00* | (2006.01) |

(52) U.S. Cl.
CPC ............. *A61B 5/742* (2013.01); *H05K 5/15* (2025.01); *A61B 2560/0406* (2013.01); *A61B 2560/0443* (2013.01)

(58) Field of Classification Search
CPC ....... A61B 5/00; A61B 5/021; A61B 5/02141; A61B 5/742
See application file for complete search history.

(56) References Cited

U.S. PATENT DOCUMENTS

| | | | | |
|---|---|---|---|---|
| 5,195,022 | A | | 3/1993 | Hoppal et al. |
| 6,049,813 | A | * | 4/2000 | Danielson .......... G06K 7/10881 |
| | | | | 714/E11.14 |
| 6,221,012 | B1 | * | 4/2001 | Maschke ................ A61B 5/002 |
| | | | | 600/509 |
| 10,539,977 | B2 | * | 1/2020 | Eslava .................. G06F 1/1632 |
| 11,204,622 | B2 | * | 12/2021 | Lund .................... A61B 5/7445 |
| 2001/0048585 | A1 | * | 12/2001 | Imsand ................. G06F 1/1607 |
| | | | | 361/679.09 |
| 2007/0293954 | A1 | * | 12/2007 | Pfingsten ............. H01R 13/514 |
| | | | | 361/728 |
| 2012/0118773 | A1 | | 5/2012 | Rayner |
| 2015/0351704 | A1 | * | 12/2015 | Kiani .................... G08B 13/22 |
| | | | | 361/679.29 |
| 2015/0359429 | A1 | * | 12/2015 | Al-Ali .................. A61B 5/6826 |
| | | | | 600/300 |
| 2016/0166321 | A1 | | 6/2016 | Amsler |
| 2016/0249468 | A1 | * | 8/2016 | Laster .................. H05K 5/0217 |
| 2020/0029823 | A1 | * | 1/2020 | Dong ...................... A61B 5/742 |

FOREIGN PATENT DOCUMENTS

| | | | |
|---|---|---|---|
| CN | 201859385 U | | 6/2011 |
| CN | 102918703 A | | 2/2013 |
| CN | 103 156 579 A | | 6/2013 |
| CN | 103156574 A | | 6/2013 |
| CN | 103156576 A | | 6/2013 |
| CN | 103156584 A | | 6/2013 |
| CN | 204119701 U | | 1/2015 |
| CN | 204425327 U | | 6/2015 |
| CN | 204671151 U | | 9/2015 |
| CN | 204995440 U | | 1/2016 |
| CN | 205359451 U | | 7/2016 |
| CN | 206303982 U | | 7/2017 |
| JP | 5974103 B2 | | 8/2016 |
| WO | WO 2014/041679 A1 | | 3/2014 |
| WO | WO 2016/081815 A1 | | 5/2016 |

OTHER PUBLICATIONS

United States Patent and Trademark Office, U.S. Appl. No. 16/283,573, Office Action dated Dec. 22, 2021, 20 pages.
E.P. Patent No. 3,505,055 A1, Anticipation/Obviousness in View of J.P. Patent No. 5,974,103 B2 ("Hideyuki Momomi"), Aug. 23, 2016, pp. 1-27.
E.P. Patent No. 3,505,055 A1, Anticipation/Obviousness in View of U.S. Patent No. 20160166321 A1, ("Phillip Amsler"), Jun. 16, 2016, pp. 1-27.
Third Party Observation for application No. EP20170842954, Sep. 9, 2021, p. 1.
EP17842954.4, Communication pursuant to Rule 114(2) EPC, Sep. 29, 2021, p. 1.
Communication pursuant to Article 94(3) EPC issued in Application No. 17842954.4, mailed May 7, 2025, 6 pages.

* cited by examiner

MEDICAL DEVICE

CROSS-REFERENCE TO RELATED APPLICATIONS

This application is a continuation of U.S. application Ser. No. 16/283,573, filed on Feb. 22, 2019, for MEDICAL DEVICE, which is a continuation of PCT Application No. PCT/CN2017/098692, filed Aug. 23, 2017, titled MEDICAL DEVICE, each of which is incorporated herein by reference.

TECHNICAL FIELD

The present disclosure relates to medical devices, and in particular to a medical device that is able to quickly switch configurations for different scenarios.

BACKGROUND

In conventional medical devices, it is sometimes beneficial to respectively connect multiple components to a housing, and the housing usually uses a split-type plastic housing. The plastic housing is impacted by the capability to make a mold and the processes of production and installation. The housing is thus generally divided into a front housing component, a rear housing component and other components assembled together.

Because there are many components, the whole housing is also divided into a large number of blocks, resulting in an unaesthetic appearance of the whole machine, such that beautifying lines or mating lines need to be added at the mated positions for improving the appearance. It is beneficial to design a special structure for connecting several components when they are assembled simultaneously.

General structural connections usually use screws, snap-fit fasteners, etc., and the connections are easily damaged by force. In particular, when replacing internal components and during maintenance, the connection structure needs to be disassembled and assembled frequently, and the connections are easily damaged by force to cause failure or is damaged by falling, which affects the normal use of the medical device.

Moreover, a stressed plastic part may be cracked after wiping with an existing medical cleaning and disinfecting agent. To solve the cracking problem, plastic materials with better chemical resistance are generally used in the existing market, resulting in high production costs.

Moreover, a conventional medical device generally uses a functional module of a standard configuration or an optional configuration of various parameters (ECG module\SPO2, module\TEMP, module\CO2 module, etc.), and the medical device is structurally designed with the maximized configuration, resulting in a relatively large volume of the medical device, which makes it inconvenient to transfer in a hospital, let alone on a battlefield or in a field rescue.

What is needed is a medical device that facilitates easy and

SUMMARY OF THIS DISCLOSURE

One aspect of the present disclosure includes a medical device comprising a housing, a combined modular structure formed by connecting a board card and an interface panel to a main bracket; a first opening provided on the housing for an insertion of the combined modular structure; a first securing structure for securing the combined modular structure to the housing; a screen assembly having a display function; a second opening provided on the housing for mounting the screen assembly; and a second securing structure for securing the screen assembly to the housing.

The screen assembly may include a screen body and a reinforcing member for reinforcing and supporting the screen body.

A first elastic buffer member may be provided between a lateral side of the reinforcing member and an inner wall of the second opening and/or between a lateral side of the screen body and an inner wall of the second opening.

The reinforcing member may include a supporting surface capable of being connected to a back side of the screen body, and a concave-convex structure capable of being mated with the housing.

The first securing structure or the second securing structure may include a securing pin, a screw or a snap-fit fastener, and the housing is provided with a structure capable of being correspondingly mated with the securing pin, the screw or the snap-fit fastener.

The screen assembly may be connected to the housing via a transverse locking member, with a locking direction of the transverse locking member being perpendicular to a direction in which the screen assembly is inserted into the second opening.

The second securing structure comprises may include a second snap-fit part arranged on at least one side surface of the screen assembly, and a mating portion may be correspondingly provided on the housing in a position enabling the mating portion to be mated with the second snap-fit part, and the screen assembly may be fixedly connected to the housing via the transverse locking member passing through the second snap-fit part.

The second securing structure may include a first snap-fit part arranged on one side of the screen assembly and a second snap-fit part arranged on the opposite side of the screen assembly, the second securing structure further comprises a slot arranged on one side of the second opening and configured to be mated with the first snap-fit part, and a securing pin arranged on the opposite side of the second opening and mated with the second snap-fit part.

The combined modular structure may further include a functional module connected to the main bracket via a damping apparatus.

The main bracket may be provided with a hanging hole, the damping apparatus may include a hanging part capable of being mated with the hanging hole, the main bracket may be provided with a fixing strut, and the damping apparatus may further include a hanging sleeve sheathed on the fixing strut;

Alternatively, the damping apparatus may include a second damping member arranged around or/and at the bottom of the functional module.

In other embodiments, a non-interference clearance is provided around the functional module, and the damping apparatus includes a second damping member arranged at the bottom of the functional module;

In one configuration, the damping apparatus is provided with a raised part making elastic contact with the main bracket;

In one embodiment, the damping apparatus includes an elastic tightening member for tightening opposite sides of the main bracket and the functional module towards each other.

The combined modular structure may further include a functional module, a main battery is provided in the housing, and the main bracket includes a shared compartment for accommodating either one of an auxiliary battery and the functional module.

The main bracket may be further fixedly provided with a thermal isolation compartment for accommodating a battery or accommodating the functional module.

A surface of the housing may be provided with at least one exposed window, and a part of the thermal isolation compartment extends to the exposed window; or/and a thermal isolation member is provided in the housing, and the thermal isolation member is connected to the thermal isolation compartment.

The thermal isolation compartment may include a compartment body comprising a main body part capable of being configured for accommodating an internal object and an exposed part that is exposed from the exposed window.

The thermal isolation compartment may further include a compartment cover connected to the compartment body, and the connection between the compartment cover and the compartment body may be provided with a sealing member; or/and at least one side of the compartment cover is provided with a reinforcing structure.

The exposed part may be provided with a venting groove, the exposed part may be provided with an exposed plate, and the exposed plate may be capped over the venting groove and partially expose the venting groove. Alternatively, an edge frame of the exposed window of the housing may block the venting groove from the above and partially exposes the venting groove.

One side of the venting groove may be provided with a blood pressure measurement air inlet, or/and the venting groove includes at least one bend.

The thermal isolation compartment may be perpendicularly and fixedly connected to the reinforcing member at the back side of the screen assembly, and the thermal isolation compartment and the reinforcing member may be fixedly connected to the main bracket or the housing.

The thermal isolation compartment and the reinforcing member may be respectively connected to the main bracket, so that the thermal isolation compartment, the reinforcing member and the main bracket form a support frame.

A plurality of circuit boards in the board card and the interface panel may be respectively fixed on the respective surfaces of the main bracket to form a frame structure, and a cavity is defined inside the frame structure.

The medical device may be connected to a medical module connection base. The medical module connection base may include an input/output interface. The input/output interface may include one or more of an AC input socket, a VGA socket, a multifunctional interface and a USB interface. The board card may include a connection interface corresponding to the input/output interface.

The housing includes may include at least two openings, and the two lateral sides having the openings may be perpendicular and adjacent to each other.

The medical device provided by the present disclosure is simple and convenient to disassemble and assemble with high efficiency to facilitate installation and replacement of different components to form different configurations, so that the medical device can quickly switch configurations for different scenarios. The disclosed medical device has better anti-vibration, waterproof and anti-drop performances.

BRIEF DESCRIPTION OF THE DRAWINGS

The drawings in the following description are merely some of the embodiments of the present disclosure and are intended to be exemplary rather than limiting.

DETAILED DESCRIPTION

Embodiments of the present disclosure will be further described below in detail in conjunction with the accompanying drawing. It should be understood that the particular embodiments described herein are merely intended to explain the present disclosure, and is not taken to limit the present disclosure.

It is to be noted that when an element is referred to as being "fixed to" or "arranged at" a further element, it can be directly on the further element, or an intermediate element may be present simultaneously. When an element is referred to as being "connected to" a further element, it can be directly connected to the further element, or an intermediate element may be present simultaneously.

It should also be noted that orientation terms, such as the left, right, upper and lower, in the illustrated embodiments of the present disclosure are merely relative concepts or referenced to the normal use state of the product, and should not be considered as having limitations.

Figure 1:
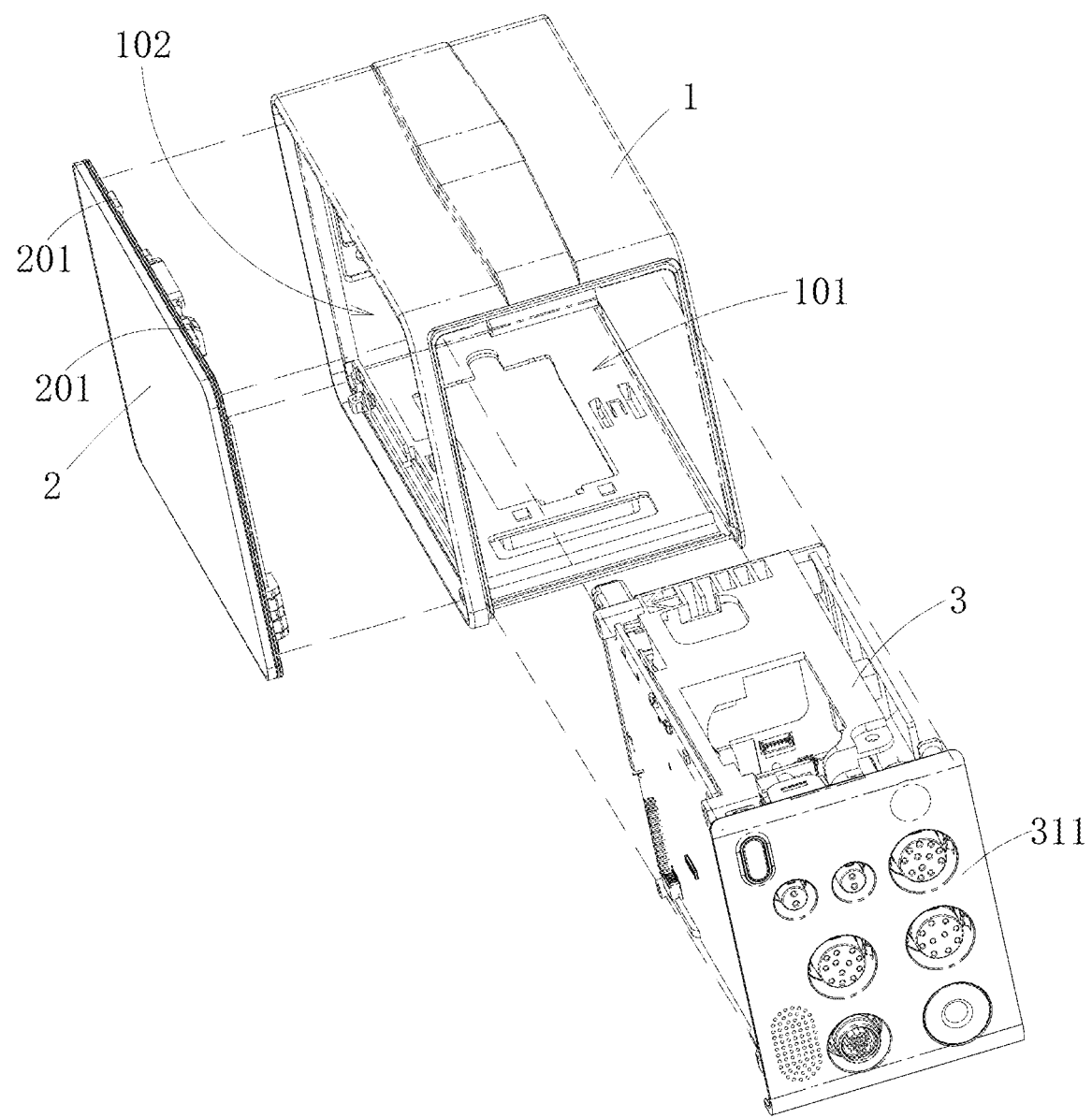
FIG. 1 is a first schematic perspective exploded diagram of a medical device.
Figure 2:
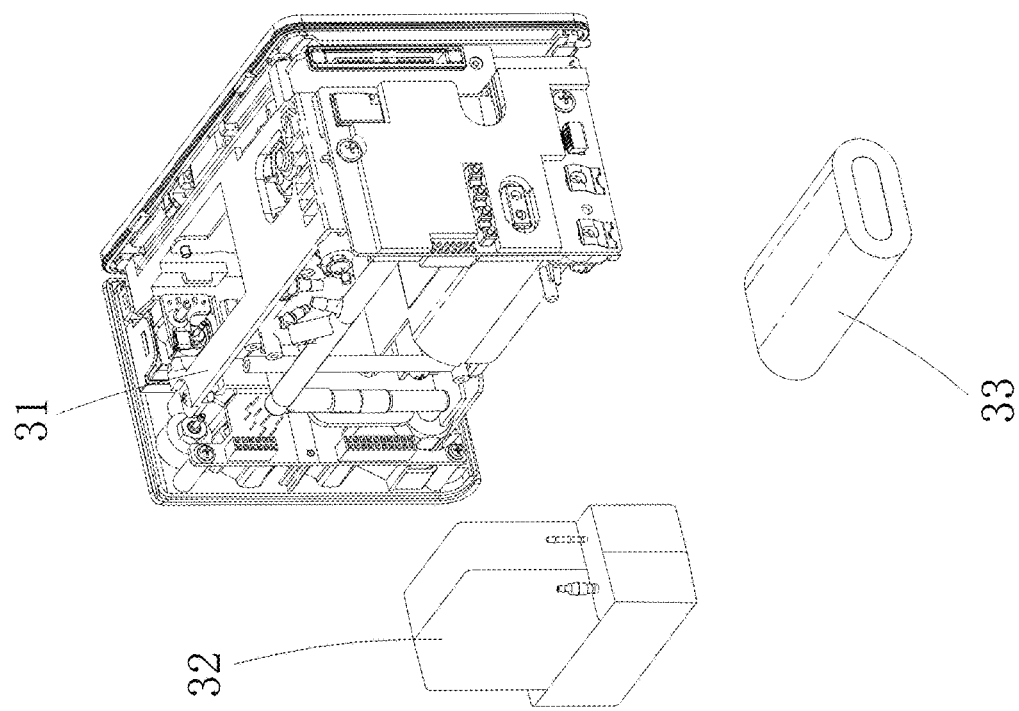
FIG. 2 is a second schematic perspective exploded diagram of the medical device.
Figure 2:
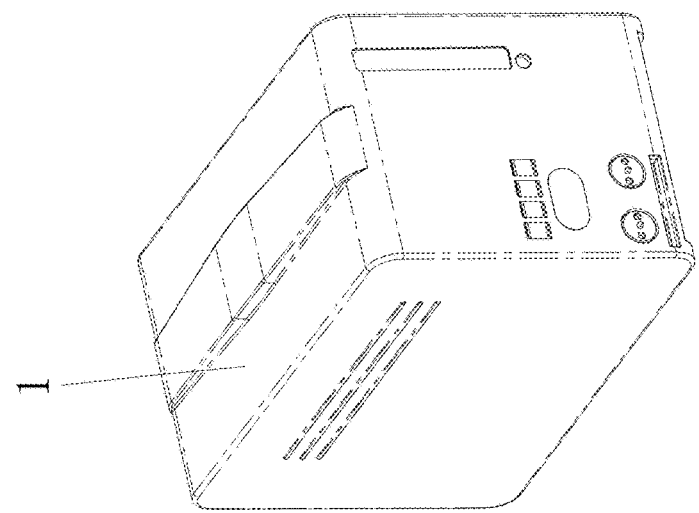

Referring to FIGS. 1 and 2, in one embodiment, a medical device is provided including a housing 1, which is designed to connect components, such as a board card (not shown)

and an interface panel 311, to a main bracket 31 and integrate the components to form a combined modular structure 3.

The board card may include a main control board card, a parameter board card, a connection board card and other members. In this way, the assembly of the main bracket 31 and other related components can be directly performed on the production line before the assembly of the whole machine of the medical device. This improves the assembly precision between the components and reduces the assembly cost. In addition, this increases the reliability of the connection between the components.

Additionally, the housing 1 is provided with a first opening 101 for insertion of the combined modular structure 3 into the housing 1. To ensure the fixing of the combined modular structure 3, the medical device of this embodiment is further provided with a first securing structure for securing the main bracket 31 on the combined modular structure 3 to the housing 1. Accordingly, instead of the component-based separation for the housing 1, the components are connected, outside the housing 1, to the main bracket 31 and integrated into the combined modular structure 3 as a whole, so that the assembly is not limited by the space of the housing 1. This is convenient for assembly to facilitate the modular testing and debugging.

In a specific arrangement, one end of the combined modular structure 3 is inserted into the first opening 101, and the other end of the combined modular structure 3 can be correspondingly capped over the first opening 101. In other words, an end face of the combined modular structure 3 can be used as an end face of the medical device. During the disassembly and assembly of the combined modular structure 3, there is no need to separate housing 1 or to design a special structure for the assembly and connection of the housing 1, so that there is no problem of damage and failure of the connections between the housing 1 and the snap-fit fastener. Moreover, since the housing 1 can be defined as an integrated structure, the housing 1 has seamlessly fitted appearance to achieve strong sense of wholeness, and the whole machine has a reliable structure, pleasing appearance and may be waterproof and dustproof.

The combined modular structure 3 including the main bracket 31 and the board card and other components fixed on the main bracket 31 can be integrally inserted into the housing 1 or removed from the housing 1 via the first opening 101, so that the disassembly and assembly process is simple and convenient, and the disassembly and assembly efficiency is high so as to facilitate installation and replacement of different components to form different configurations, so that the medical device can quickly switch configurations to apply to different scenarios.

Therefore, medical device provided by this embodiment can be quickly installed and replaced and does not need to be structurally designed with the maximized configuration, so that the medical device is relatively small in overall dimension. This makes it convenient for transportation, and can be applied to situations such as battlefield and field rescue.

The main bracket 31 may be connected to the functional module 32 in addition to the board card and the interface panel 311. The medical device provided by this embodiment may be a monitor, and the functional module 32 may be a carbon dioxide module and of course other application modules. The functional module 32 may be mounted on the main bracket 31 by using a snap-fit structure so as to meet different application scenarios. It can be understood that the medical device of this embodiment can also be another instrument, and the functional module thereof can be selected as needed.

The first securing structure may be a securing pin, a screw or a snap-fit fastener, and the housing 1 is provided with a structure capable of being correspondingly mated with the securing pin, the screw or the snap-fit fastener, so as to avoid the combined modular structure 3 from being released from the housing 1.

Figure 3:
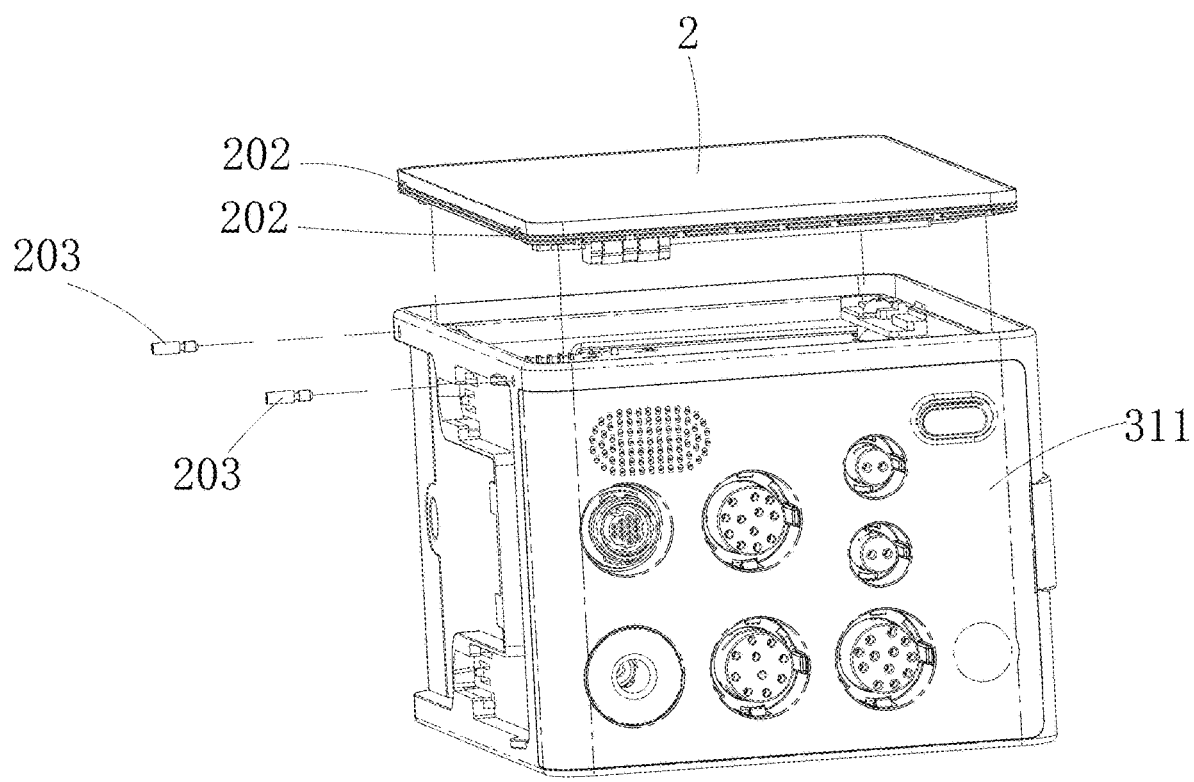
FIG. 3 is a schematic perspective exploded diagram of the medical device.
Figure 4:
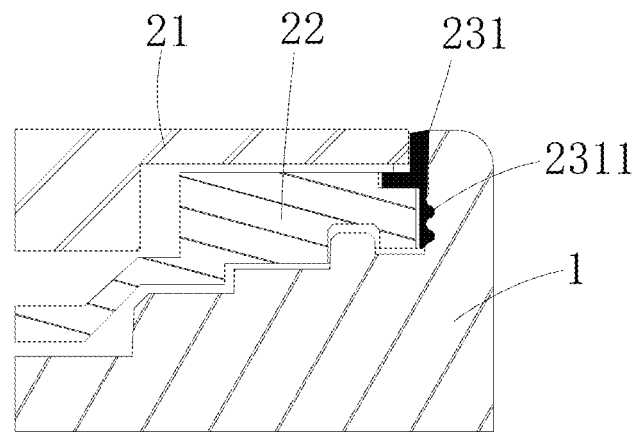
FIG. 4 is a schematic partial cross-sectional diagram of a screen assembly, which adopts a first shock resistance and waterproofing solution, in the medical device.

Referring to FIGS. 1 to 3, the medical device of this embodiment further includes a screen assembly 2 having a display function. The housing 1 is further provided with a second opening 102 for mounting the screen assembly 2, and in order to facilitate the fixing of the screen assembly 2, the medical device of this embodiment is further provided with a second securing structure for securing the screen assembly 2 to the housing 1.

In one embodiment, the outer surface (display face) of the screen assembly 2 should not protrude from the open face of the second opening 102. For example, in one embodiment, the outer surface of the screen assembly 2 may be flush with the open face of the second opening 102. Alternatively, in another embodiment, the outer surface of the screen assembly 2 may also be recessed relative to the open face of the second opening 102. The above structure should ensure that no structural member is exposed after the screen assembly 2 is assembled.

Moreover, in one embodiment, an outer edge of the screen assembly 2 is embedded in the second opening 102 and then abuts against an inner side of the second opening 102. Moreover, the outer surface of the screen assembly 2 is not provided with a second securing structure mounted perpendicular to the end face of the second opening 102 and a mating structure for mounting the second securing structure.

Referring to FIGS. 1 to 3, in one embodiment, the housing 1 may be an integral-type housing, such as an integrated frame structure. The first opening 101 may be provided on one side of the housing 1, and the second opening 102 may be provided on the other side of the housing 1. In this embodiment, the first opening 101 is provided on a lateral side of the housing 1, and the second opening 102 is provided on a front side of the housing 1. For example, in one embodiment, the end faces of the first opening 101 and the second opening 102 are perpendicular to each other.

In the housing 1, a guiding part for guiding the combined modular structure 3 to be inserted into the housing 1 may be provided, so that the combined modular structure 3 can be smoothly inserted into the housing 1 or withdrawn from the housing 1. The guiding part may be a linear guide rail, a linear guide groove, or one of a convex block and a concave block. The guiding part and the combined modular structure 3 may form a slideway mating structure, so that the combined modular structure 3 can be easily pulled from the housing or the combined modular structure 3 can be guided to extend into the housing 1 via the first opening 101.

The guiding part may be very short, e.g., being arranged on the end face of the first opening 101, or extending from the end face of the first opening 101 toward the interior of the housing 1 by a predetermined distance which is smaller than the length of the housing in the corresponding direction. The slideway mating structure formed by the guiding part and the combined modular structure 3 may be a sliding groove-sliding rail mating structure, a protrusion-groove mating structure and the like.

A buffer member may be provided between the housing 1 and the main bracket 31. The buffer member may be an elastic rubber member or the like, so as to further improve the anti-vibration performance of the whole machine.

In order to allow the combined modular structure 3 to be conveniently inserted into the housing 1, in one embodiment, a guiding structure is provided inside the housing 1.

In one embodiment, the second securing structure may be a securing pin, a screw or a snap-fit fastener, and the housing 1 is provided with a structure capable of being correspondingly mated with the securing pin, the screw or the snap-fit fastener.

In one embodiment, as shown in FIGS. 1 to 3, the second securing structure may include a second snap-fit part 202 arranged on a side surface of the screen assembly 2, and a corresponding mating portion is provided on the housing 1 at a position mated with the second snap-fit part 202, e.g., a fixing hole position provided on a surface of one side of the second opening 102.

The second securing structure may further include a securing pin 203 that is arranged on a surface of one side of the second opening 102 and is mated with the second snap-fit part 202, with a fixed mounting direction of the securing pin 203 being approximately parallel to the end face of the second opening 102. In order to firmly fix the screen assembly 2 on the housing 1 and to allow the outer surface of the screen assembly 2, from the front view, to be not provided with a second securing structure mounted perpendicular to the end face of the second opening 102 as well as a mating structure for installation of the second securing structure. In the above embodiment, at least two structures in which the second snap-fit part 202 and the corresponding mating portion of the side surface of the second opening 102 are fixedly mounted on the side surface may be provided on the four side surfaces of the screen assembly 2, e.g., the second snap-fit parts 202 are provided on at least two side surfaces of the screen assembly 2, and accordingly and correspondingly, it is also beneficial to provide mating portions, on the second opening 102, correspondingly mated with the second snap-fit parts 202. For better stable fixing, in the second snap-fit parts 202 arranged on the at least two side surfaces of the screen assembly 2, at least two are oppositely arranged.

In addition, in one embodiment, another method may be used to stabilize the arrangement of the screen assembly 2, and from the front view, the outer surface of the screen assembly 2 is not provided with a second securing structure mounted perpendicular to the end face of the second opening 102 as well as a mating structure for installation of the second securing structure.

For example, the second securing structure may include a first snap-fit part 201 arranged on a surface of one side of the screen assembly 2 and a second snap-fit part 202 arranged on a surface of the opposite side of the screen assembly 2, the first snap-fit part 201 may be a raised snap-fit fastener, and the second snap-fit part 202 may be a securing groove. The second securing structure further includes a slot arranged on one side of the second opening 102 and used to be mated with the first snap-fit part 201 as well as a securing pin 203 arranged on the other side opposite to the second opening 102 and mated with the second snap-fit part 202, with the fixed mounting direction of the securing pin 203 being approximately parallel to the end face of the second opening 102, e.g., the securing pin 203 may be a transverse locking member 210.

During installation, the screen assembly 2 is first assembled by fitting the two first snap-fit parts 201 (snap-fit fasteners) at the top into the slots and inserting and locking the two securing pins 203 at the bottom into the securing grooves, so that it is simple to assemble and easy to disassemble, and the installation process thereof is easy and convenient.

The screen assembly is connected to the housing 1 via the transverse locking member, with the locking direction of the transverse locking member being perpendicular to the direction in which the screen assembly 2 is inserted into the second opening 102, and it can also be understood that the mounting direction of the transverse locking member is parallel to the end face of the second opening 102.

Referring to FIGS. 1 to 4, the screen assembly 2 includes a display screen body 21 and a reinforcing member 22 for reinforcing and supporting the screen body 21. The reinforcing member 22 may be a rigid member, and may be a reinforcing frame, a reinforcing plate or a reinforcing bar made of metal, which may be of a rectangular frame shape, a rectangular plate shape or a strip shape. In the illustrated structure, the reinforcing member 22 is of a rectangular frame shape and is connected to the back side of the screen body 21, and the reinforcing member 22 serves to support, fix and reinforce the screen body 21 to improve the structural strength of the screen body 21.

The outer side wall of the reinforcing member 22 may be mated with the inner side wall of the second opening 102, and can be used as a fixing structural member between the screen body 21 and the housing 1, which can ensure a successful installation of the screen assembly 2 and can also reinforce the strength of the housing 1. Since the screen assembly 2 can be separately disassembled, it is convenient for maintenance and replacement.

The reinforcing member 22 may be adhered to the screen body 21 through an adhesive, and the adhesive may be an adhesive layer, which has reliable bonding and a certain buffering and damping effects.

In order to further improve the anti-vibration performance of the screen assembly 2, as shown in FIGS. 1 to 4, as a first anti-vibration solution of the screen assembly 2, a first elastic buffer member 231 is provided between the lateral side of the reinforcing member 22 or/and the lateral side of the screen body 21 and the inner wall of the second opening 102. For example, the first elastic buffer member 231 may be arranged on the lateral side of the reinforcing member 22, or may be arranged on the lateral side of the screen body 21.

The first elastic buffer member 231 has a certain elasticity and may be a rubber ring or a rubber strip, and the lateral side of the first elastic buffer member 231 may be provided with a convex rib 2311 to further improve the buffering and waterproofing effects. The reinforcing member 22 is used as a metal skeleton, the first elastic buffer member 231 is arranged surrounding the lateral side of the reinforcing member 22 or the screen body 21, and the first elastic buffer member 231 is pressed and deformed to protect the screen assembly 2 in a buffer manner, so that the screen assembly 2 meets the requirements of drop, impact and vibration.

Figure 5:
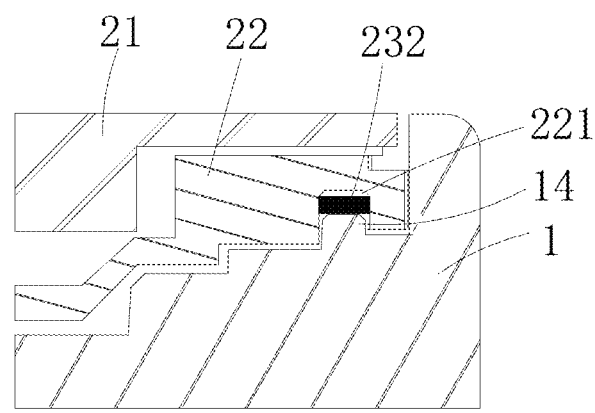
FIG. 5 is a schematic partial cross-sectional diagram of a screen assembly, which adopts a second shock resistance and waterproofing solution, in the medical device.

As a second anti-vibration solution of the screen assembly 2, referring to FIG. 5, the front side of the screen body 21 is a display surface for observing the display results of electrical signal output by the screen assembly 2. The reinforcing member 22 includes a supporting surface that can be connected to the back side of the screen body 21, and a concave-convex structure that is mated with the housing 1, and the concave-convex structure may be provided on the other side of the reinforcing member 22. A second elastic buffer member 232 is arranged in the concave-convex structure, and the second elastic buffer member 232 is pressed and deformed.

In one embodiment, the reinforcing member 22 is provided with a groove 221, and the housing 1 is provided with a raised part 14 extending into the groove 221, and a second elastic buffer member 232 is arranged between the groove 221 and the raised part 14, which also makes the screen assembly 2 meet the requirements of drop, impact and vibration.

The second anti-vibration solution can be implemented alone or simultaneously with the first anti-vibration solution. The first elastic buffer member 231 or the second elastic buffer member 232 is in interference-fit with the housing 1 to achieve a waterproofing effect. By means of triple damping by the housing 1, the first elastic buffer member 231, the second elastic buffer member 232 and the reinforcing member, the screen assembly 2 can realize that the machine of 1.0 KG falls at a height of 1.2 meters without damage, the impact resistance is good, and the whole machine can meet the requirements of helicopter transportation.

The main bracket 31 of this embodiment may be connected to the functional module 32 in addition to the board card and the interface panel 311. The medical device provided by this embodiment may be a monitor, and the functional module 32 may be a carbon dioxide module and of course other application modules. The functional module 32 may be mounted on the main bracket 31 by using a snap-fit structure so as to meet different application scenarios. It can be understood that the medical device of this embodiment can also be another instrument, and the functional module thereof can be selected as needed.

Figure 6:
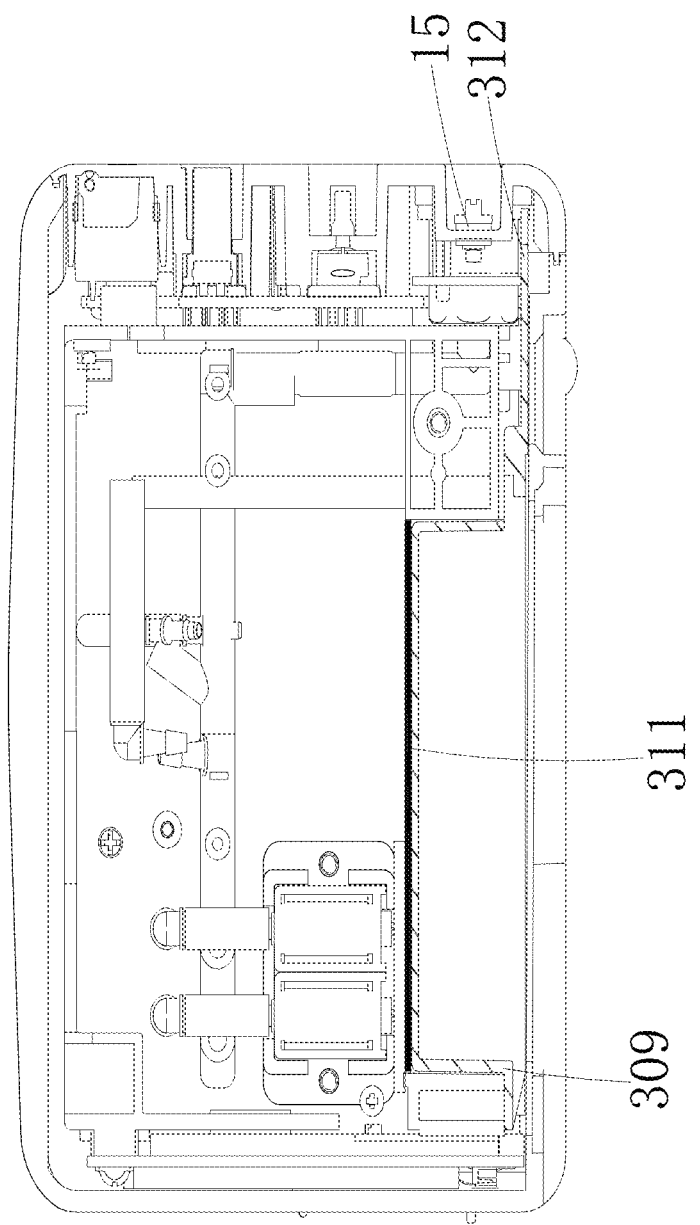
FIG. 6 is a schematic plane diagram of a main bracket in the medical device.

Referring to FIG. 6, the main bracket 31 of this embodiment is further fixedly provided with a thermal isolation compartment 309 for accommodating the battery or the functional module 32. The thermal isolation compartment 309 may be a metal chamber, e.g., the side wall of the thermal isolation compartment 309 may be made of metal. A thermal isolation member 311 is arranged in the housing 1, and the thermal isolation member 311 may be connected to the main bracket 31 to form a thermal isolation and separation space. One end of the thermal isolation member 311 is connected to the side wall of the thermal isolation compartment 309, and the other end of the thermal isolation member 311 is connected with a heat dissipating surface shell 15 to improve the heat dissipation performance in the thermal isolation compartment 309, so that the battery or the functional module 32 in the thermal isolation compartment 309 can operate within a suitable temperature range.

The thermal isolation member 311 may be made of a material having a high thermal conductivity, e.g., a metal material such as copper or aluminum, and the thermal isolation member 311 may also be a heat pipe. In one embodiment, the thermal isolation compartment 309 is a battery compartment, and a main battery 13 can be arranged in the thermal isolation compartment 309. Two or more thermal isolation compartments 309 may also be provided, and the functional module 32 may also be arranged in the thermal isolation compartment 309.

The thermal isolation compartment 309 is connected in a lap joint with the housing 1 (e.g., the housing 1 may be made of plastic made of a heat dissipating material), so that the heat of the battery is conducted as much as possible to the outside of the whole machine, which facilitates cooling of the battery. In this way, the internal heat dissipation problem can be solved by reducing the battery temperature. Compared with the solutions using heat dissipation by air convection, heat dissipation by metal heat sink, heat dissipation by silica gel and the like in conventional approaches, the medical device provided by the embodiment isolates regions having different heat requirements and then dissipates heat for specific regions, so that the heat dissipation effect is improved by the material change of the housing 1 without adding a specific heat dissipation module. As a result, heat dissipation is more targeted, the product cost is low, the heat dissipation can be performed through the structural member of the housing 1, and the appearance effect is better.

Referring to FIG. 6, in this embodiment, a thermal isolation material layer 312 may be arranged on the side wall and the end of the thermal isolation compartment 309. The thermal isolation material layer 312 may be a plastic member thermal isolation layer, the battery and other thermal elements in the thermal isolation compartment 309 are thermally isolated by the thermal isolation compartment 309 and the thermal isolation material layer 312, so that the battery compartment alone becomes an air-conditioned room, which is not affected by the heating device inside the machine, thereby further improving the thermal isolation effect.

Figure 12:
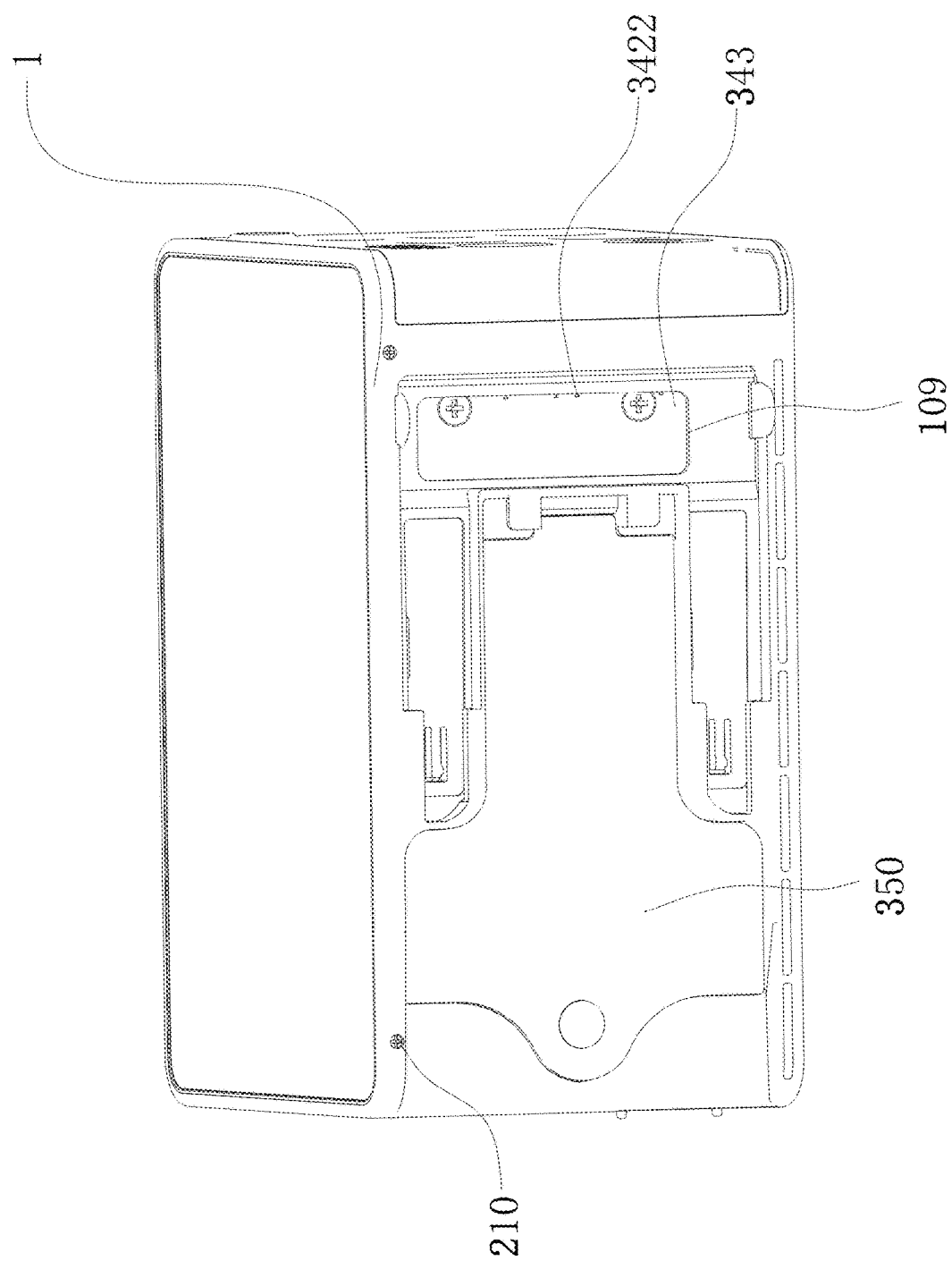
FIG. 12 is a perspective assembly schematic diagram of a medical device.
Figure 13:
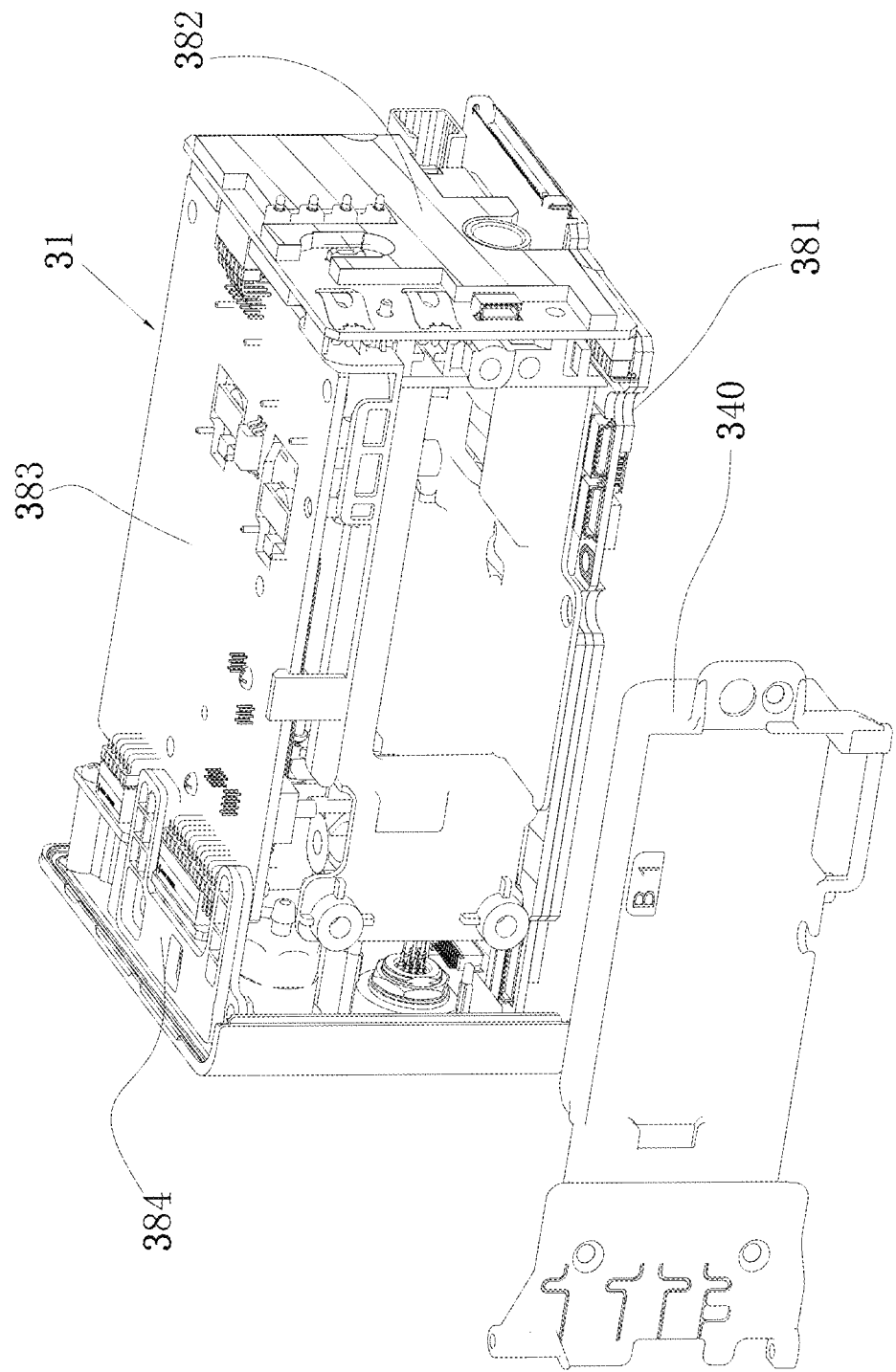
FIG. 13 is a schematic perspective exploded diagram of a main bracket and a compartment body of a thermal isolation compartment in the medical device.

Referring to FIG. 12, in other embodiments, at least one exposed window 109 is arranged on a lateral side of the housing 1, and a part of the thermal isolation compartment 309 extends to the exposed window 109. For example, a part of the thermal isolation compartment 309 is connected in a lap joint with the housing 1 and exposes a part of the thermal isolation compartment 309 (e.g., an end face or the like) to the exposed window 109. This can directly dissipate heat by radiation to the outside. The heat dissipation path is short, and the battery or other components in the thermal isolation compartment 309 can achieve better heat dissipation performance, so that the battery (main battery) or other components in the thermal isolation compartment 309 can work within a suitable temperature range. This further improves the stability and reliability of the device.

Especially in a miniaturized device which is small and compact and has high heat dissipation requirements, such a structural design can make the device meet the requirements of heat dissipation in the miniaturized application. The thermal isolation compartment 309 can be made of a metal or a high thermal conductivity plastic or composite material for better heat dissipation.

In one embodiment, a double-compartment structure of a shared compartment 310 and a thermal isolation compartment 309 is designed, the thermal isolation compartment 309 is one of the compartments and can hold a battery pack, and if the compartment (the thermal isolation compartment 309) does not hold a battery, it can hold a carbon dioxide module or other required functional modules.

Referring to FIGS. 12 to 15, optionally, the exposed window 109 may be arranged at a suitable position on the bottom, the back side, the lateral side or the top side of the housing 1. In one embodiment, in one embodiment, the thermal isolation compartment 309 may include a compartment body 340, and still further, the thermal isolation compartment 309 may further include a compartment cover 350 connected to the compartment body 340.

The compartment body 340 can be made of a heat dissipating material such as a metal, and the compartment cover 350 can be made of a different material from the compartment body 340. The main battery or the functional module may be arranged in the compartment body 340.

The compartment body 340 includes a main body part 341 that can be used to accommodate the internal object as well as an exposed part 342 that is exposed to the exposed window 109. The main body part 341 may adopt a semi-closed or closed frame structure. The surface of the exposed part 342 is higher than the plane of the edge of the main body part 341 to form a stepped shape, or the plane of the edge of the main body part 341 and the surface of the exposed part 342 are on the same plane. The compartment cover 350 may be connected to the main body part 341 of the compartment body 340 by way of locking of a snap-fit fastener or/and a locking member.

Figure 14:
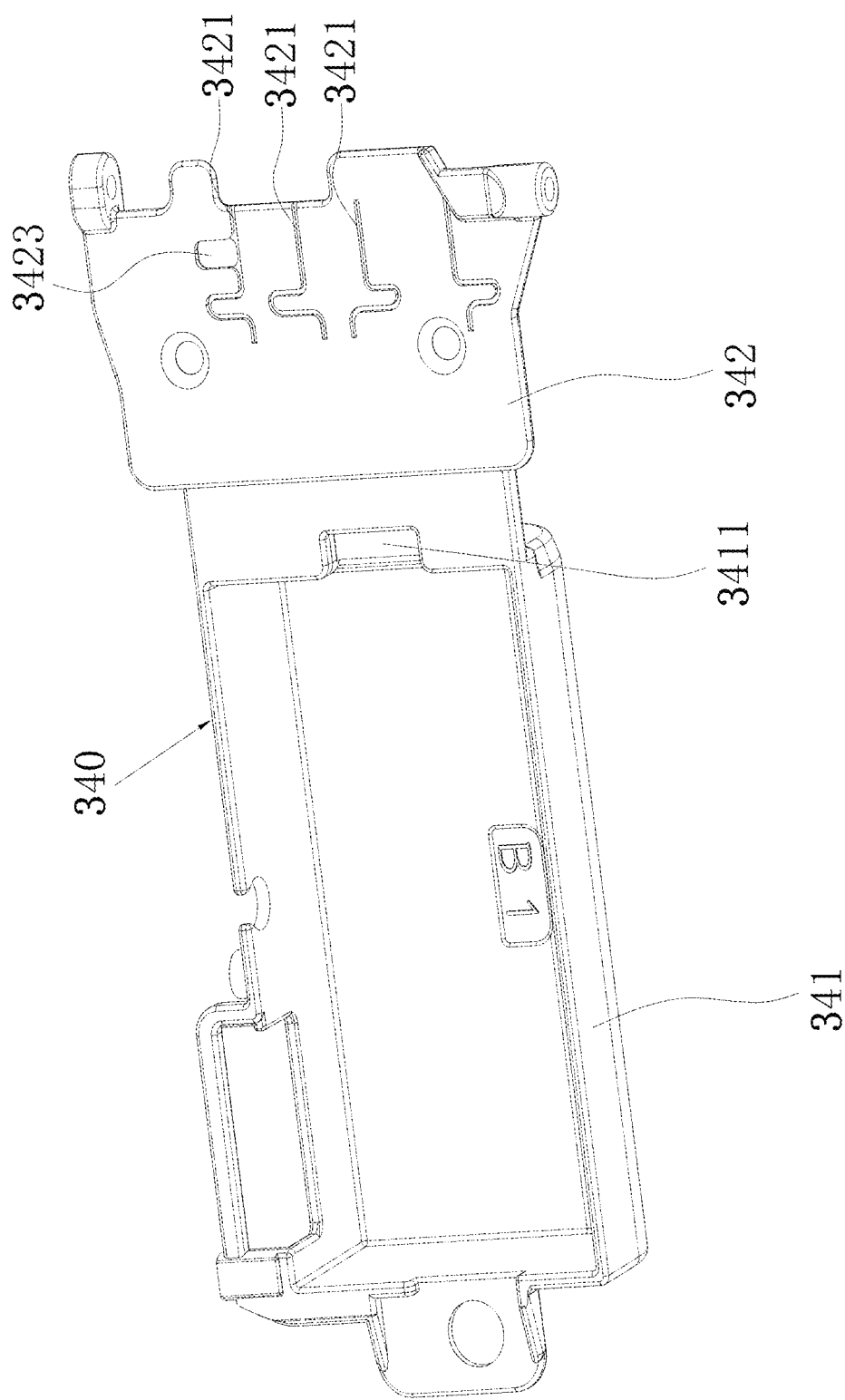
FIG. 14 is a perspective schematic diagram of a compartment body of a thermal isolation compartment in a medical device.
Figure 15:
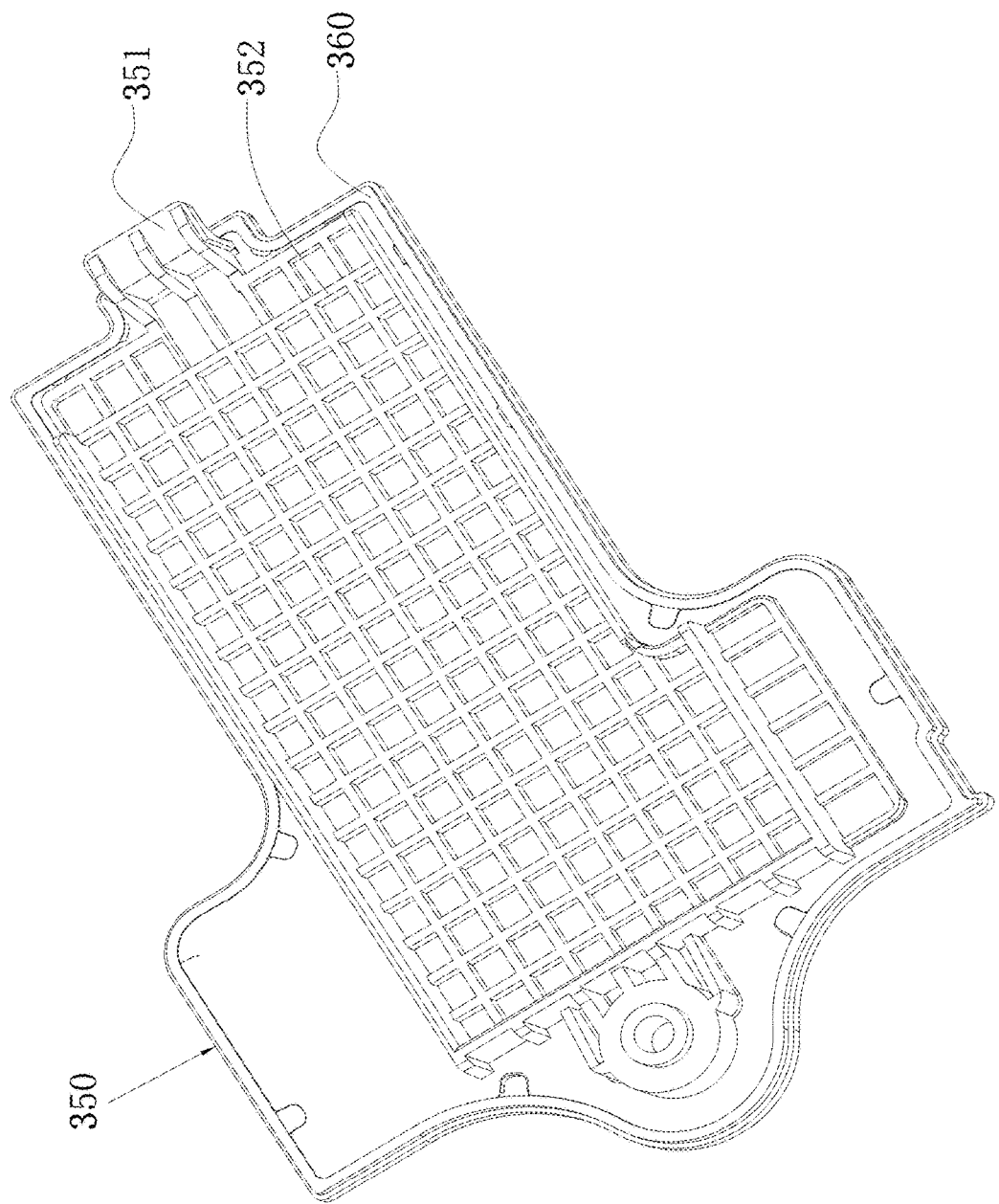
FIG. 15 is a perspective schematic diagram of a compartment cover of a thermal isolation compartment in a medical device.

Referring to FIGS. 14 and 15, the compartment cover 350 has an insertion pin part 351 at one end, the insertion pin part 351 being inserted into an insertion hole 3411 of the compartment body 340, and the other end of the compartment cover 350 is connected to the compartment body 340 via a locking member (bolt). A sealing member 360 may be provided at the connection between the compartment cover 350 and the compartment body 340. The sealing member 360 may be a seal ring or a sealant or the like.

In the illustrated structure, the sealing member 360 is arranged between the compartment cover 350 and the main body part 341. The seal ring may be a rubber ring, which can be embedded in a preset rubber ring groove of the compartment cover 350 or the compartment body 340, is easy to assemble and can completely seal the opening position of the compartment body 340, so that the sealing effect is good, and the grade of waterproof can be up to IP44.

Continuing to refer to FIG. 15, optionally, one side or both sides of the compartment cover 350 is/are provided with a reinforcing structure. The reinforcing structure may be a reinforcing rib 352. The reinforcing rib 352 may be integrally formed on the end face of the compartment cover 350 and arranged intersecting vertically and horizontally. The compartment cover 350 has a high structural strength and is not easily deformed. The inner or outer surface of the compartment body 340 may also be provided with reinforcing ribs 352 intersecting vertically and horizontally to further increase the structural strength of the thermal isolation compartment 309.

When the device is in a state of being placed normally, the compartment cover 350 is located at the bottom of the whole device. By providing the above-mentioned reinforcing structure, it can withstand the impact of the main battery or the functional module and other components in the compartment body 340, the compartment cover 350 is not easily deformed or damaged, and the reliability of device is better, thereby improving the anti-vibration and anti-drop properties of the whole device.

Continuing to refer to FIGS. 12 to 15, optionally, in one embodiment, the exposed part 342 is provided with a venting groove 3421, and the venting groove 3421 is used for communicating the outside with the interior of the housing 1 for air circulation. Furthermore, after the combination of one or more of the above components is completed, a sealed inner cavity can be formed in the housing 1. For example, in one embodiment, the housing 1 is combined with the combined modular structure 3, the screen assembly 2 and the compartment cover 350 to form a sealed inner cavity in the housing 1. The exposed part 342 is provided with a venting groove 3421, and the venting groove 3421 communicates with the outside air and the sealed inner cavity.

One side of the venting groove 3421 may be provided with a blood pressure measurement air inlet. The exposed part 342 may be attached with an exposed plate 343. The exposed plate 343 can be capped over the venting groove 3421, and only a part of the venting groove 3421 (e.g., the front end 3422) can be exposed. The exposed plate 343 may be a metal member and may pass through the exposed plate 343 by means of a screw, and the exposed part 342 is locked to the main bracket 31 or the housing 1. The exposed plate 343 may also be replaced by the edge frame of the exposed window 109 of the housing 1. When the exposed window 109 covers the exposed part 342, a part of the venting groove 3421 is blocked, and only a part of the venting groove 3421 (e.g., the front end 3422) is exposed, as shown in FIG. 12.

The venting groove 3421 may have at least one bend to improve waterproof performance while ensuring ventilation. In one specific application, the venting groove 3421 may be of a curved shape, a polygonal shape or the like, e.g., a regular curved shape such as an S-shape or a wavy shape or an irregular curved shape. The front end 3422 of the venting groove 3421 is exposed, e.g., the front end of the venting groove 3421 communicates directly with the outside air, so that the venting groove 3421 can also serve as a heat dissipating passage while venting. In the illustrated structure, the front end 3422 of the venting groove 3421 is located at the edge of the exposed part 342.

It can be understood that the front end 3422 of the venting groove 3421 may also be located at other suitable positions, e.g., at the middle of the exposed part 342 and the like. One or more venting grooves 3421 may be provided. One side of the venting groove 3421 is provided with a blood pressure vent hole 3423, and the blood pressure vent hole 3423 communicates with the venting groove 3421, and can serve as an air inlet for blood pressure measurement while being waterproof. Blood pressure measurement can be achieved by a blood pressure measurement module connected to the main bracket 31. The blood pressure measurement module, as a functional module, may be arranged in the shared compartment 310 or in the thermal isolation compartment 309.

In order to increase the grade of waterproof of the whole device to the IP44 level, in addition to the aforementioned structures, the structural design can also be considered. For example, in one embodiment, the exposed part 342 and the exposed window 109 are located on one lateral side of the housing 1, and the lateral side is parallel and adjacent to the end face where the first opening is located. When the screen assembly 2 is on the front side, the exposed part 342 and the exposed window 109 are located on the bottom side of the housing 1.

In addition, the housing 1, as a whole, is a sealed structure in addition to the first opening 101, the second opening 102, the exposed window 109 and the opening mated with the compartment cover 305. In order to better realize the sealed structure, the housing 1 adopts an integrally formed structure. The second opening is located at the side surface of the housing 1, and the connection (such as the first opening 101) between the combined modular structure 3 and the housing 1 is subjected to a waterproof sealing process by a sealing rubber ring or the like, and the connection (such as the second opening 102) between the screen assembly 2 and the housing 1 is also subjected to a waterproof sealing process by a sealing rubber ring or the like, so that the whole device can achieve the waterproof effect of IP44 in addition to the beneficial ventilation and heat dissipation effects.

As shown in FIG. 14, in one embodiment, on the thermal isolation compartment 309, the compartment body 340 includes a main body part 341 that can be used to accommodate the internal object. The end face of the main body part 341 connected in lap joint with the compartment cover 350, together with the exposed part 342, is located on the same lateral side of the housing 1 as the exposed window 109, the lateral side being parallel and adjacent to the end face where the first opening is located. When the screen assembly 2 is on the front side, the exposed part 342 and the exposed window 109 are located on the bottom side of the housing 1.

Such an approach can significantly improve waterproofing, save space utilization and reduce the need for external sealing members in addition to the beneficial ventilation and heat dissipation effects. In one embodiment, the housing 1 has only three lateral sides with an opening, while the other three sides have no opening. In particular, the three sides with an opening are perpendicular and adjacent to each other.

For the exposed window 109, the compartment cover 350 and the interface panel 311 can be arranged at the same end face. Therefore, in one embodiment, the housing 1 has at least two openings, and the two lateral sides with an opening are perpendicular and adjacent to each other. One of the openings is for placing the screen assembly 2, and the other opening is for providing an insertion interface for such as the exposed window 109, the main body part 341 and a module combination interface.

Figure 16:
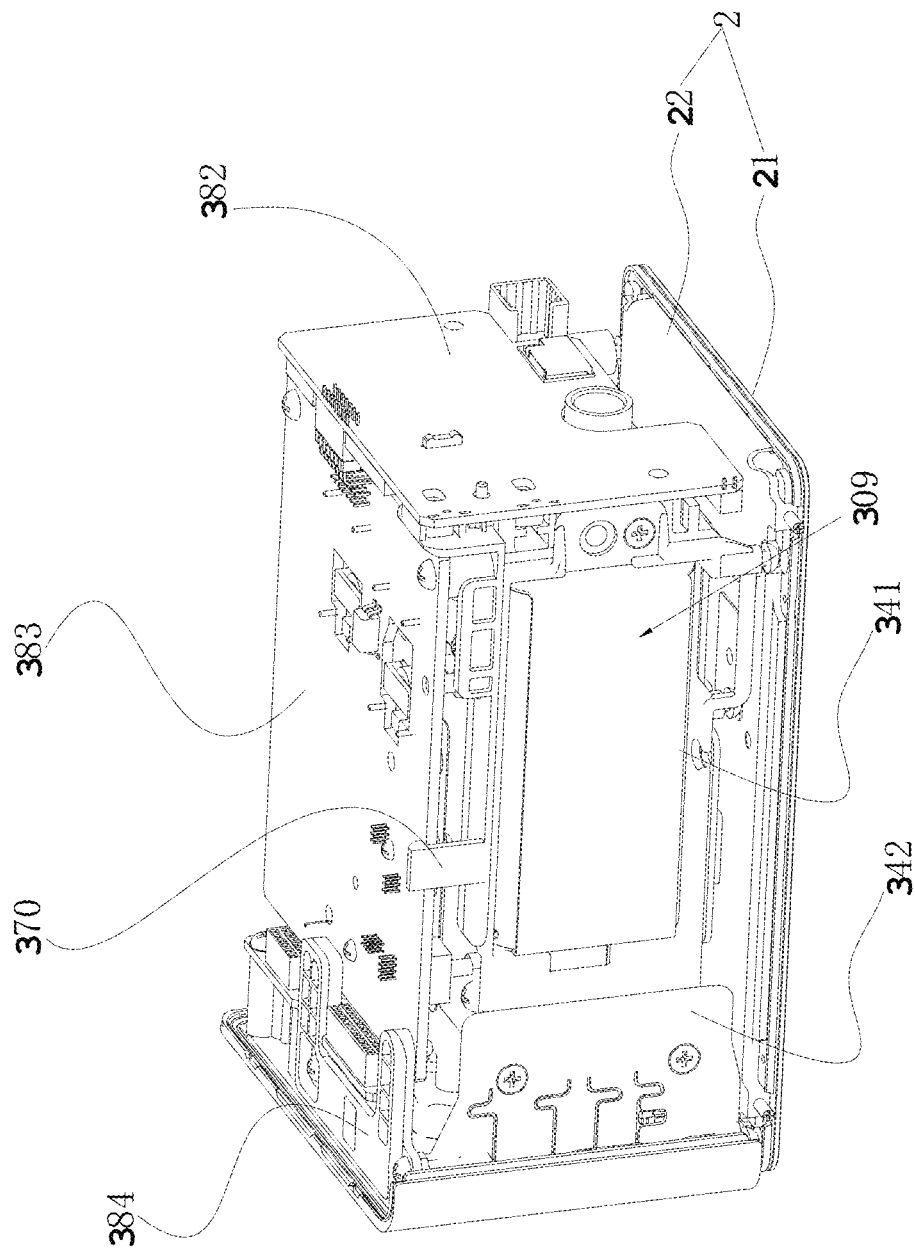
FIG. 16 is a perspective schematic diagram of a main bracket in a medical device.
Figure 17:
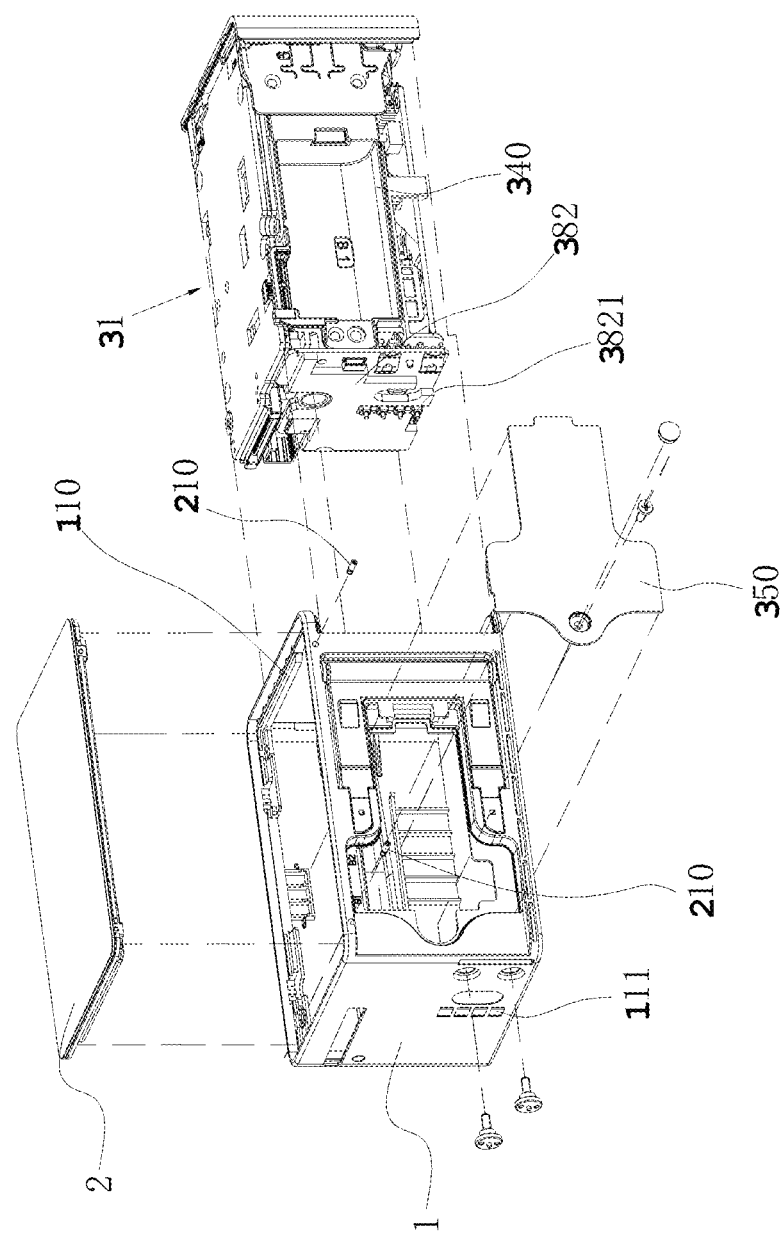
FIG. 17 is a schematic perspective exploded diagram of a medical device.
Figure 18:
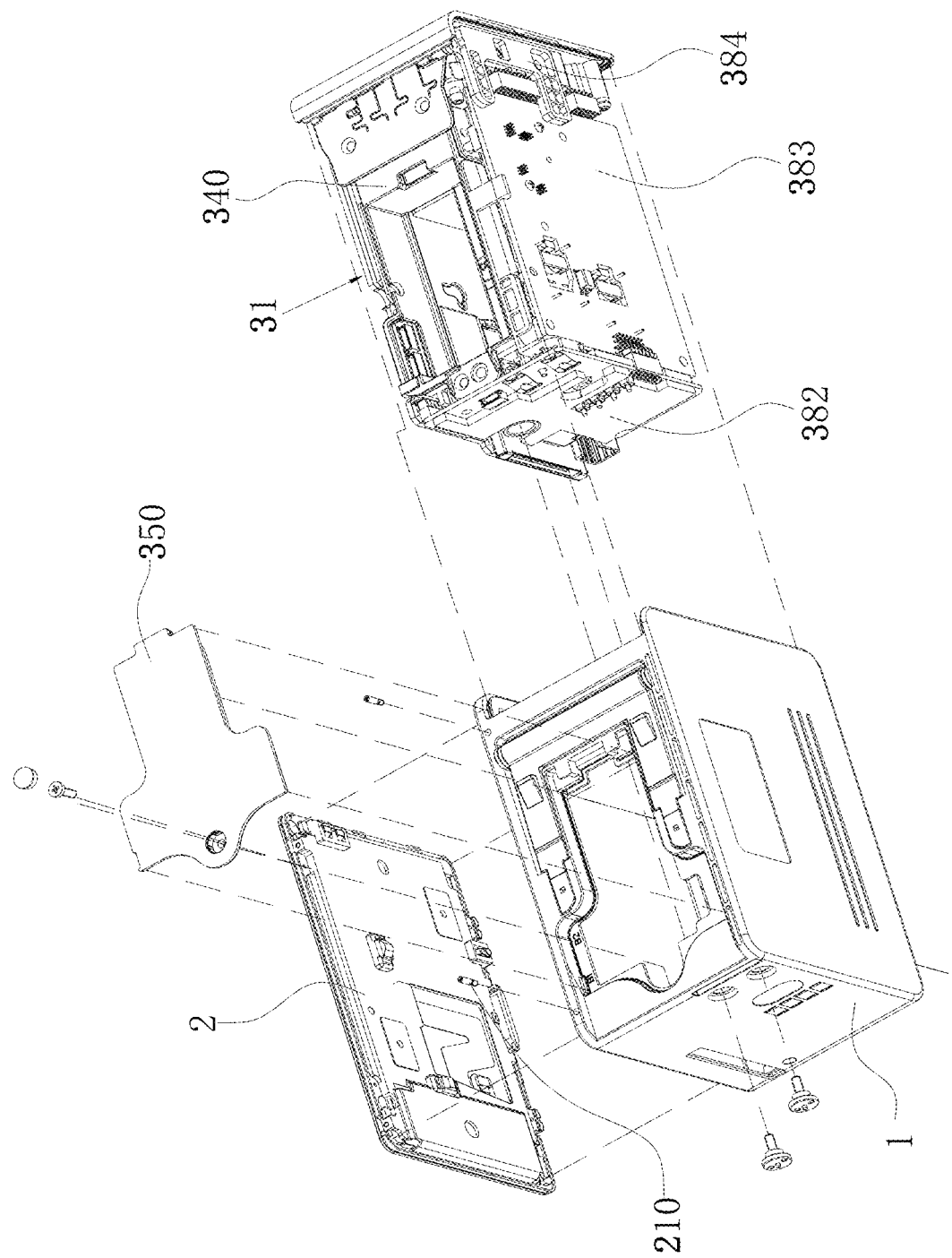
FIG. 18 is a schematic perspective exploded diagram of a medical device.

Referring to FIGS. 16 to 18, in order to improve the anti-drop performance of the device, optionally, the thermal isolation compartment 309 is fixedly connected to the reinforcing member 22, and the thermal isolation compartment 309 and the reinforcing member 22 are arranged perpendicular to each other. In other words, the thermal isolation compartment 309 is adjacent and perpendicular to the front side where the reinforcing member 22 and the display screen body 21 are located.

As described above, the reinforcing member 22 is connected to the back side of the screen body 21, and can support, fix and strengthen the screen body 21 to improve the structural strength of the screen body 21. Moreover, the thermal isolation compartment 309 and the reinforcing member 22 can both be metal members, and the thermal isolation compartment 309 and the reinforcing member 22 are fixedly connected with each other and both are connected and fixed to the main bracket 31 or the housing 1, thereby forming a stable support structure.

In addition, a reinforcing bracket 370 may also be used, the thermal isolation compartment 309 and the reinforcing member 22 are fixedly connected to the reinforcing bracket 370, so that the thermal isolation compartment 309, the reinforcing member 22 and the reinforcing bracket 370 form a stable supporting frame, which can effectively protect the display screen body 21 to prevent damage caused by impact or drop. The reinforcing bracket 370 may be a metal member or a plastic member. In one embodiment, in the combined modular structure, the board card (not shown) and the interface panel 311 include at least three circuit boards, e.g., a first circuit board 381, a second circuit board 382 and a third circuit board 383 in FIGS. 13 and 16.

The main bracket 31 is connected with the first circuit board 381, the second circuit board 382 and the third circuit board 383 on different lateral sides of the main bracket 31. The first circuit board 381, the second circuit board 382 and the third circuit board 383 are respectively fixed at the respective lateral sides of the main bracket 31 so as to form a frame structure, and the interior of the frame structure forms a cavity for arranging the shared compartment 310 and the thermal isolation compartment 309 and the like to place the functional module 32, the battery and the like.

In this embodiment, by respectively fixing multiple circuit boards on the respective lateral sides of the main bracket 31 so as to form a frame type fixing structure having a cavity inside, the structure is compact to obtain the highest space utilization, and the volume of the whole device is reduced, so that the volume is reduced to less than 249 mm×97 mm×111 mm and the weight is less than 1.4 KG. In particular, in one embodiment, the whole device has a volume of less than 150 mm*103 mm*81 mm and a weight of less than or equal to 1.2 KG. In the case of such a small-volume design, the housing 1 can be selected to use a waterproof and anti-corrosive material. In order to better improve the overall anti-drop property, the aforementioned structural reinforcement design between the thermal isolation compartment 309 and the reinforcing member 22 can be utilized to enhance the anti-drop property of the whole device, and the whole machine can meet the requirements of dropping from 1.2 meters without damage. On this basis, in one embodiment, the main bracket 31 is also connected with a reinforcing connector 384. The first circuit board 381 may be a main control board, the second circuit board 382 may be an infrared board, and the third circuit board 383 may be a parameter board. The first circuit board 381, the second circuit board 382, the third circuit board 383, the interface panel 311 and the reinforcing connector 384 may be connected to the aforementioned support frame to enclose a closed cavity structure, thereby further improving the stability and reliability of the whole machine.

In one embodiment, the screen assembly 2 is located on the front side of the device and is oriented toward the user. The first circuit board 381 is located on the front side of the main bracket 31 and located at the back side of the screen assembly 2, the interface panel 311 is located at one end of the main bracket 31 and can be capped at the first opening 101 of the housing, and the second circuit board 382 is located at the other end of the main bracket 31 and extends deep inside the housing 1.

The third circuit board 383 is located at the back side of the main bracket 31. The thermal isolation compartment 309 is located at the bottom of the main bracket 31, and the first circuit board 381, the second circuit board 382 and the third circuit board 383 may be locked to the main bracket 31 by locking members (such as screws).

The reinforcing connector 384 may be locked to the support frame by a locking member (such as a screw), and the reinforcing connector 384 can be pressed against the third circuit board 383. The reinforcing connector 384 may be a U-shaped plastic or metal member. The reinforcing bracket 370 is fixedly connected to the main bracket 31, and the compartment body 340 of the thermal isolation compartment 309 is connected to the reinforcing bracket 370.

The reinforcing bracket 370 may have a snap-fit fastening arm for fastening the third circuit board 383. In this way, the interface panel 311 (the face board), the parameter board, the infrared board and the main control board are respectively fixed on the four sides of the main bracket to form a stable bracket structure (the main bracket 31), which is formed into a whole and then inserted into the plastic housing 1, then the screen assembly 2 is fixed, and the screen assembly 2 is fixed by a lateral bolt 210.

Through the above arrangement, the plastic bracket 31 is reinforced with two metal members, i.e., a battery compartment 310 (a metal member) and a screen support member (a metal member), to form a stable metal support frame. In addition, the support frame is enclosed by the first circuit board 381, the second circuit board 382, the third circuit board 383 and the reinforcing connector 384 to form a closed cavity so as to strengthen the strength of the whole structure and fully protect the screen assembly 2.

Optionally, as shown in FIG. 18, the screen assembly 2 may be connected to the housing 1 via a transverse locking member (which may be a lateral bolt 210). The lateral side of the second opening 102 is a narrow-side housing, and the lateral bolt 210 laterally secures the screen assembly 2 from the lateral side, that is, the securing direction of the lateral bolt 210 is perpendicular to the direction in which the screen assembly 2 is inserted into the second opening 102.

The external screen of the screen assembly 2 can occupy or substantially occupy the area of the front side of the housing 1, its screen-to-body ratio is high, and in the case where the device sizes are equivalent, the information displayed by the screen assembly 2 is more comprehensive and specific. The display screen body 21 of the screen assembly 2 can be made of one-piece glass, which can realize a narrow-border or borderless appearance, which is beautiful and elegant.

In one embodiment, the inner side of the housing 1 may also be fixedly connected with a plastic liner support 110, and the plastic liner support 110 can adopt an integrally formed rectangular frame structure, which can improve the buffering performance and impact resistance of the device.

The medical device of this embodiment can be connected to a carrying case to facilitate transportation, expansion, data interaction and the like. The carrying case may also be referred to as a medical module connection base. The medical module connection base may be the medical module connection base disclosed in PCT Publication No. WO 2014169554A1, which is incorporated herein by reference.

The medical module connection base may also be medical module connection bases of other specifications and other types. The shape of the compartment door is matched in shape with the slide rail and is fixed in the external medical module connection base. The medical module connection base is provided with an input/output interface, and the input/output interface includes one or more of an alternating-current input socket, a VGA socket, a multifunctional interface and a USB interface. The second circuit board 382 (i.e., the infrared board) is provided with a connection interface 3821 corresponding to the above input/output interface. The lateral side of the housing 1 may be provided with a hole site 111 matching the interface 3821 to expose the connection interface 3821 so as to facilitate the interface connection with the carrying case.

Figure 7:
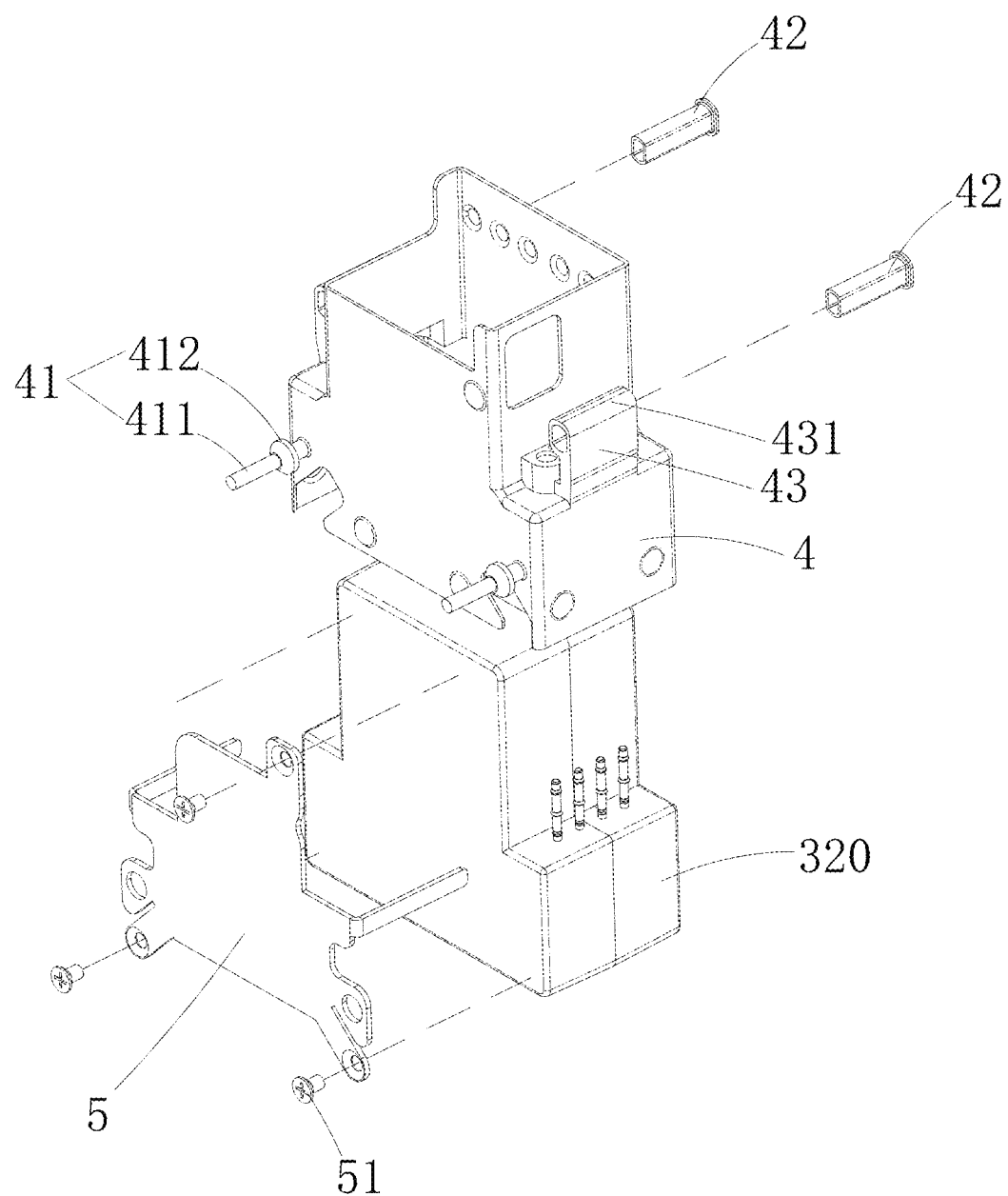
FIG. 7 is a schematic perspective exploded diagram of a carbon dioxide module, a damping cushion member and a hanging bracket in a medical device.
Figure 8:
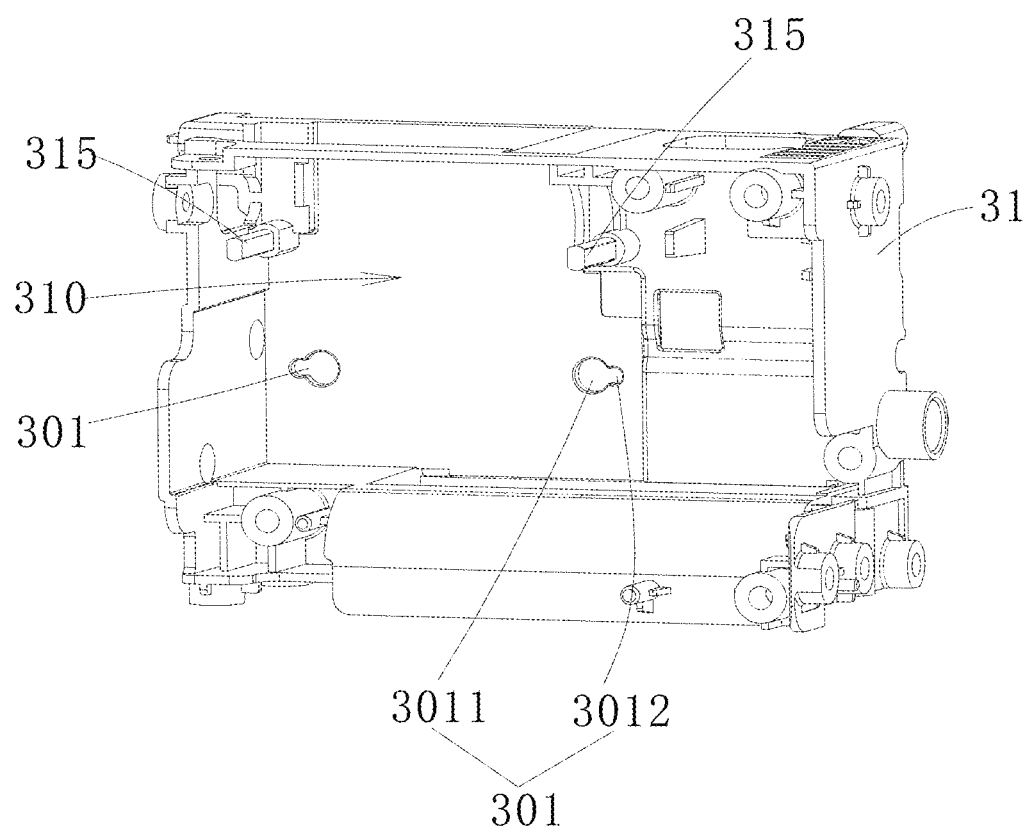
FIG. 8 is a perspective schematic diagram of a main bracket in a medical device.
Figure 9:
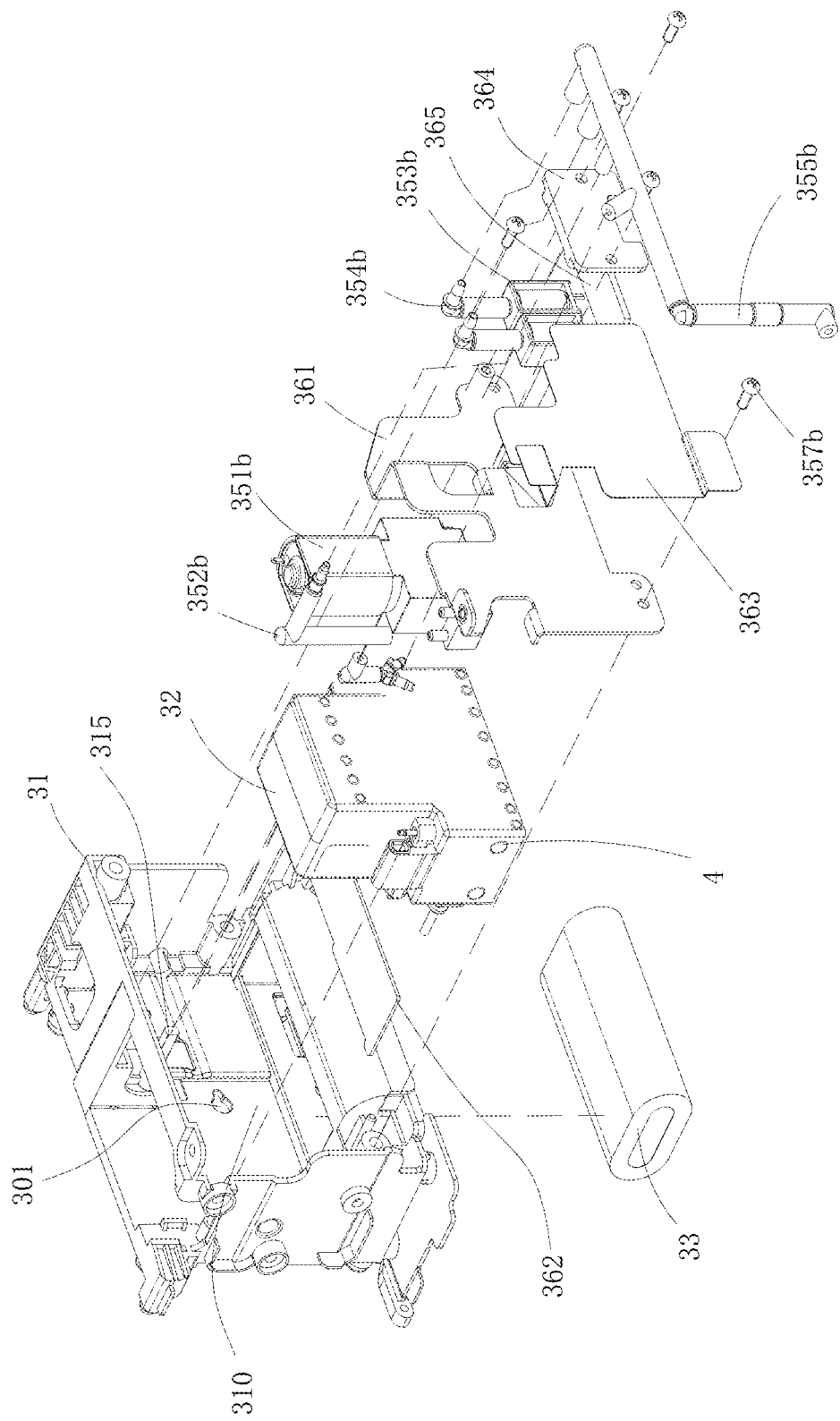
FIG. 9 is a schematic perspective exploded diagram of a medical device when a functional module configuration is used.

Referring to FIGS. 7 to 9, in order to improve the reliability of the use of the medical device, the functional module 32 is connected to the main bracket 31 via a damping apparatus, the medical device may be a monitor, and the functional module 32 may be a module for generating vibration during operation or other modules. In this embodiment, the functional module 32 takes a carbon dioxide module as an example.

Under the premise that the structures of the housing 1 and the functional module 32 are not changed, the damping apparatus is connected between the functional module 32 and the main bracket 31, so that the configuration of the functional module 32 can be added in the inherent space structure of the monitor, thereby expanding the application range of the monitor, and arranging the corresponding damping structure while adding the application function thereof so as to perform damping treatment for the functional module 32. As a result, the influence of the vibration of the function module 32 itself on the accuracy of the functional module 32 can be avoided, and the influence of the vibration of the functional module 32 itself on the reliability of other components can also be avoided, which is beneficial to ensure the normal operation of the monitor and facilitate the transportation and use of the monitor.

The functional module 32 is elastically connected to the main bracket 31 in a hanging connection manner via the damping apparatus, and the hanging connection manner can be arranged in a compact and narrow space, thereby having a better damping effect. In one embodiment, the functional module 32 can be elastically connected to the main bracket 31 via a two-point or multi-point hanging connection through the damping apparatus so as to reduce and absorb the vibration of the functional module 32 to avoid the influence of such vibration on other components, thereby realizing the vibration isolation effect.

The damping apparatus may be sheathed, as a whole, on the outer side of the functional module 32, or may be adhered to the functional module 32 by an adhesive. Alternatively, the damping apparatus may be locked to the functional module 32 by the locking member. Certainly, the damping apparatus may also be connected to the functional module 32 by other means.

As one embodiment of the damping apparatus, referring to FIG. 7, the damping apparatus is connected to the functional module 32, and is elastically connected to the main bracket 31 in a multi-point hanging connection manner, specifically as follows: the main bracket 31 is provided with a hanging hole 301, the damping apparatus may be elastically sheathed outside the functional module 32, and the damping apparatus includes a hanging part 41 mated with the hanging hole 301; or/and, the main bracket 31 is provided with a fixing strut 315, and the damping apparatus further includes a hanging sleeve 42 sheathed on the fixing strut 315. In this way, a multi-point hanging structure is formed, and the vibration isolation effect is good.

In one embodiment, the damping apparatus includes a first damping member 4 sheathed outside the functional module 32, and the first damping member 4 may be an elastic sleeve, such as a silicone sleeve. The hanging part 41 is integrally formed or connected to the first damping member 4, the connecting part 43 is integrally formed or connected to both sides of the first damping member 4, and the connecting part 43 has a hanging structure 431, the hanging sleeve 42 is sheathed in the hanging structure 431, the hanging sleeve 42 may be an elastic member, and the hanging sleeve 42 may be sheathed on the fixing strut 315. By adopting the solution in which the functional module is wrapped and fixed by an elastic sleeve and is hung on both sides, without changing the functional module 32 itself, in the case of a limited space, the influence of the vibration generated by the functional module 32 on other components is greatly reduced by reducing the shape influence coefficient and reducing the rigidity and the like.

In one embodiment, the hanging holes 301 are arranged in pairs and symmetrically arranged at intervals, the hanging parts 41 are also arranged in pairs, the hanging holes 301 matches in the number and position of the hanging parts 41, the hanging part 41 includes a hanging rod 411 and a support part 412, the support part 412 is fixedly connected to or integrally formed on the hanging rod 411 to position the hanging part 411 at the position of the hanging hole 301, and the hanging hole 301 may be of a suitable shape, such as a gourd shape. In this embodiment, the hanging hole 301 includes a large hole 3011 and a small hole 3012 which are partially overlapped with each other, the hanging hole 301 is of a gourd shape, and the outer diameter of the support part 412 is greater than the outer diameter of the small hole 3012 and less than the outer diameter of the large hole 3011, that is, the support part 412 can pass through the large hole 3011 but cannot pass through the small hole 3012. When assembled, the hanging rod 411 and the support part 412 pass through the hanging hole 301 from the front side of the large hole 3011 under an external force, and after assembled, the support part 412 may be supported at the back side of the small hole 3012 under the elastic restoring force of the first damping member 4, so that the functional module 32 can be kept connected to the main bracket 31 in an elastic hanging manner, the functional module 32 is not easy to fall off, and the assembly of the damping device is simple and easy.

In one embodiment, the fixing struts 315 may be fixedly connected to the main bracket 31 by welding or integral molding or the like, and the fixing struts 315 may also be connected to the main bracket 31 by means of a detachable structure such as threaded connection.

Specifically, the first damping member 4 may be connected with a hanging bracket 5, and the hanging bracket 5 may fix the first damping member 4 to the functional module 32 and provide a force point during hanging. In this embodiment, the hanging bracket 5 is connected to the functional module 32 by means of the locking member 51 and clamps the first damping member 4 to fix the first damping member 4. The hanging bracket 5 may be stamped and formed by a metal sheet. The locking member 51 may be a screw.

The assembly process may be as follows. First, the first damping member 4 (the silicone sleeve) is sheathed on the functional module 32, and the circumference is in interference fit and held tightly. Then, the hanging bracket 5 is loaded, the hanging bracket 5 is fixed by a bolt to fix the first damping member 4, and the hanging bracket 5 can provide a force point during hanging. The hanging sleeve 42 is then sheathed on the hanging structure 431 of the first damping member 4 so as to obtain an assembled functional module assembly. Then, the hanging part 41 of the first damping member 4 is mounted to the hanging hole 301 of the main bracket 31, and then the two hanging sleeves 42 are respectively squeezed into the fixing struts 315 in an interference fit manner, so that the functional module 32 can form a multi-point hanging connection structure by means of the first damping member 4 and the main bracket 31, which has a good vibration isolation effect and a compact structure.

A second embodiment of the damping apparatus includes a second damping member (not shown) arranged around or/and at the bottom of the functional module 32; Alternatively, a non-interference clearance is provided around the functional module 32, and the damping apparatus includes a second damping member arranged at the bottom of the functional module 32. The second damping member may be an elastic member, such as an air bag, sponge or rubber. In one embodiment, the sponge can be used as the second damping member, and the functional module 32 can be wrapped with 10 mm-thick sponge at the periphery, so as to achieve the vibration isolation effect by means of the vibration absorption by the sponge. Due to the particularity of the vibration direction of the functional module 32, the above solution can be simplified to only provide a sponge at the bottom of the functional module 32, the thickness of the sponge may be 10 mm, and a gap of 2 mm or more is reserved around the functional module 32 for avoid interference, which can also achieve better vibration isolation effect.

A third embodiment of the damping apparatus may be provided with a raised part (not shown) that is in elastic contact with the main bracket 31. In one embodiment, the damping apparatus includes a damping buffer sleeve sheathed outside the functional module 32, the outer surface of the damping buffer sleeve is provided with a raised part (not shown) in elastic contact with the main bracket 31, the outer surface of the damping buffer sleeve is designed with a triangular or rectangular raised part, and then the amount of interference between the raised part and the main bracket 31 is adjusted to improve the vibration isolation effect. In addition to the silicone material, the damping buffer sleeve may also be made of other damping materials, and the interference capacity is designed according to its corresponding compression ratio, so that the functional module 32 is wrapped from four sides.

A fourth embodiment of the damping apparatus may include an elastic tightening member (not shown) for pulling the opposite sides of the main bracket 31 and the functional module 32 toward each other, that is, the functional module 32 is tensioned, at the opposite sides, to the main bracket 31 by the elastic material. The elastic tightening member may be a hanging rubber strip or the like.

In this embodiment, a buffer member (not shown) may be arranged between the housing 1 and the main bracket 31. The buffer member may be an elastic rubber member or the like to further improve the damping performance of the whole machine and the functional module 32.

Further, the main bracket 31 has a main battery compartment, a main battery 33 is arranged in the main battery compartment, and the main bracket 31 has a shared compartment 310 having either one of an auxiliary battery and the functional module 32 accommodated therein. The medical staff can choose to place an auxiliary battery or install the functional module 32 in the shared compartment 310 according to specific needs, and the auxiliary battery and the functional module 32 are mutually exclusive, that is, either one of the two can be connected to the main bracket 31, so that it is very convenient to assemble monitors of different configurations with no need to be structurally designed with the maximized configuration, and the monitor is relatively small in overall dimension, has a compact structure, is convenient for transportation, and is very convenient for use in situations such as battlefield and field rescue.

A medical device of a dual-battery configuration and a medical device configured with a carbon dioxide module as the functional module are respectively described in two embodiments below, and for convenience of illustration, only the parts related to the present embodiment are shown.

Embodiment I

In this embodiment, the functional module 32 is disposed in the shared compartment 310, and referring to FIGS. 1 to 3, the main bracket 31 is connected with a functional module compartment bracket 361 for forming a functional module compartment in the shared compartment 310, and a functional module 32 is arranged in the functional module compartment to form different functional configurations.

Referring to FIG. 9, the main bracket 31 is connected with a blocking piece 362 for separating the main battery compartment so as to prevent the heat generated during the operation of the battery from affecting the normal operation of the functional module 32.

One side of the functional module compartment bracket 361 is arranged opposite to the functional module 32, and the other side of the functional module compartment bracket 361 is attached with an insulating sheet 363 and/or a water absorbing member. The water absorbing member may be a water absorbing sponge.

The main bracket 31 may be connected to an air pump 351b, and the air pump 351b may be located on the left or right side of the functional module 32; and the air pump 351b is connected with a pump outlet air pipe 352b, the main bracket 31 is also connected with a valve body 353b, the bottom of the valve body 353b has a water absorbing member 365, and the water absorbing member 365 may be a water absorbing sponge. The main bracket 31 is connected with a valve pressing plate 364 for pressing the valve body 353b, the valve body 353b is connected with the valve outlet air pipe 354b, and the pump outlet air pipe 352b is connected to the pump outlet air pipe 354b via the center shaft pipe 355b.

The fixing struts 315 may be fixedly connected to the main bracket 31 by welding or integral molding or the like, and the fixing struts 315 may also be connected to the main bracket 31 by means of a detachable structure such as threaded connection, so that when different functional modules 32 are switched or when the auxiliary battery needs to be installed on the main bracket 31, the fixing struts 315 can be conveniently removed from the main bracket 31 even if the spatial position of the functional module or the auxiliary battery interferes with the spatial position of the fixing strut 315.

During assembly, it is confirmed that, in the main bracket 31, the fixing struts 315 for mounting the functional module 32 is arranged on the main bracket 31, a blocking piece 362 is first loaded onto the main bracket 31, and then the assembled functional module assembly is loaded into the main bracket 31. Then, the air pump 351b installed with the damping sponge and the pump outlet air pipe 352b is loaded onto the main bracket 31 and then is fastened into the functional module compartment bracket 361 and fixed by the locking member (bolt) 357b, then the insulating sheet 363 and the water absorbing member 365 are attached thereto, the valve body 353b is mounted with the valve outlet air pipe 354b and then is loaded on the functional module compartment bracket 361, and then the valve pressing plate 364 is fastened. Then the air channels are connected through a central shaft pipe 355b (functional module configuration). Finally, the main battery 33 is loaded from the bottom.

Embodiment II

Figure 10:
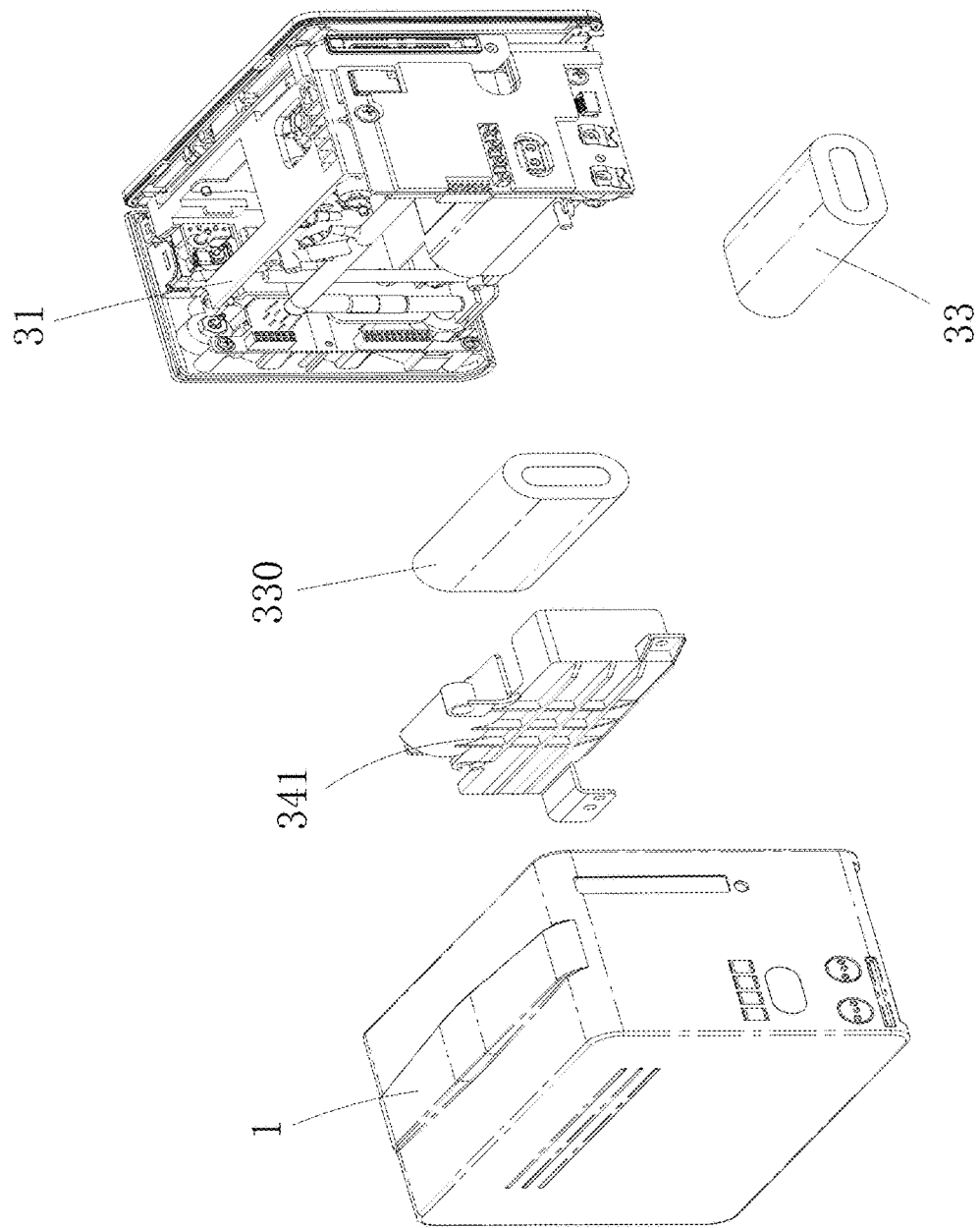
FIG. 10 is a schematic perspective exploded diagram of a medical device when a dual-battery configuration is used.
Figure 11:
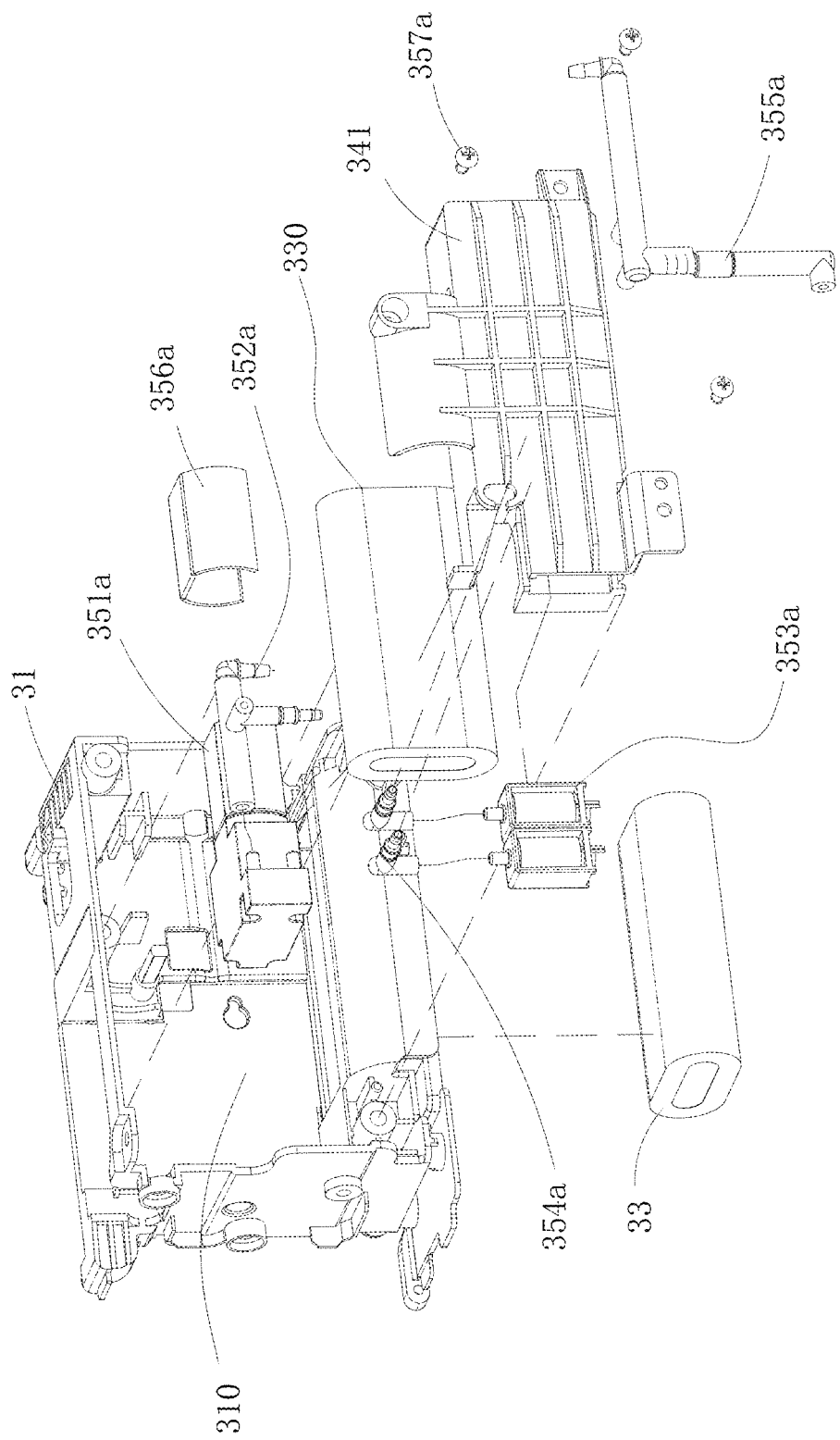
FIG. 11 is a schematic perspective exploded diagram of a medical device when a dual-battery configuration is used.

Referring to FIGS. 10 and 11, in this embodiment, an auxiliary battery 330 is arranged in the shared compartment 310, the main bracket 31 is connected with an auxiliary battery compartment bracket 341 for forming an auxiliary battery compartment in the shared compartment 310, and an auxiliary battery 330 is arranged in the auxiliary battery compartment so as to form a dual-battery configuration solution, so that the monitor can be operated continuously for a long time and can perform long-distance vital sign monitoring for a long time.

Specifically, the openings of the main battery compartment and the auxiliary battery compartment are on the same side as the first opening 101, and the openings of the main battery compartment and the auxiliary battery compartment are each provided with a battery door. Alternatively, the main battery compartment is in communication with the auxiliary battery compartment, so that the battery can be replaced and maintained from the outside without being disassembled.

As shown in FIG. 11 again, in the dual-battery configuration, the main bracket 31 is connected with an air pump 351a, the air pump 351a is located below the auxiliary battery 330, the air pump 351a is connected with a pump outlet air pipe 352a, the main bracket 31 is also connected with a valve body 353a, the valve body 353a may be of a dual-valve structure, the valve body 353a is connected with a valve outlet air pipe 354a, and the valve outlet air pipe 352a is connected to a valve outlet air pipe 354a via a central shaft pipe 355a.

With continued reference to FIG. 11, a third damping member 356a may be arranged around or/and at the bottom of the air pump 351a so as to reduce vibration and noise; and alternatively, a non-interference clearance is provided around the air pump 351a, and a third damping member 356a is provided at the bottom of the air pump 351a. The third damping member 356a may be an elastic member such as an air bag, sponge or rubber.

During assembly, if there are fixing struts for connecting the functional module 32 in the main bracket 31 and the fixing struts interfere with the related components such as the auxiliary battery 330 and the auxiliary battery bracket 341, the fixing struts can be removed from the main bracket 31 or the fixing struts can be detached from the main bracket 31, and then the air pump 351a installed with the damping sponge (the third damping member 356a) and the pump outlet air pipe 352a is loaded. After the valve body 353a is connected to the valve outlet air pipe 354a, it is first loaded into the auxiliary battery compartment bracket 341, then the auxiliary battery compartment bracket 341 is fixed to the main bracket 31 by the locking member (bolt) 357a, then the air channels are connected by the central shaft pipe 355a (the dual-battery configuration), and finally the main battery 33 and the auxiliary battery 330 are loaded from the bottom.

When the monitor is configured to have a dual-battery configuration of the main battery 33 and the auxiliary battery 330, the monitor can be operated continuously for a long time, and can perform long-distance vital sign monitoring for a long time. When the monitor is configured to have the functional configuration of the main battery 33 and the functional module 32, the monitor measurement parameters are comprehensive, and the monitor is in the dual-battery configuration and the functional module configuration, so that the main bracket 31 can be shared, the component cost is low, the configuration switch and assembly processes are simple, and no special tools are needed in the process, which is convenient to operate.

The medical device provided by this embodiment integrates the board card, the interface panel and the main bracket, and adopts the plug-in connection of the opening of the housing, so that the display screen can be mated with the housing via the assembly structure and can be separately disassembled. In this way, the combination of multiple components becomes a combination of two components, the housing can adopt an integrated structure, the housing can be assembled and connected without disassembling the housing and without designing a special structure, and there is no problem of damage and failure of the housing interface part and the snap-fit fastener. This gives the whole machine a seamless appearance, a strong sense of wholeness mated with the other members, and good waterproof and dustproof properties.

Moreover, with such an integrated structure, the processing of the housing is convenient, the production cost is low, and the assembly of the internal components of the whole machine is not limited by the space of the housing, so that the assembly process is simple, and the modular testing is convenient. The board card, the interface panel and the main bracket are integrated, and the assembly of the components can be directly completed on the production line before the assembly of the whole machine, which is advantageous for improving the assembly precision between the components, reducing the assembly cost, and effectively ensuring the reliability of the connection between the components.

Moreover, the structure disassembly and assembly process of such an integrated arrangement is simple and convenient, the disassembly and assembly efficiency are high, and different functional modules can be installed and replaced immediately to form different configurations, so that the medical device can quickly switch configurations to apply to different scenarios. The spatial size of the whole machine can be reduced to 150 mm*103 mm*81 mm, and the weight is less than or equal to 1.2 KG, which is convenient for transportation and is also convenient to use in various different situations. Further, in this embodiment, the screen assembly is detachably configured, so that maintenance and update of the product are more convenient. In addition, the screen assembly of this embodiment achieves triple damping by means of the housing, the first elastic buffer member (or the second elastic buffer member) and the reinforcing member, thereby effectively ensuring the reliability of the working of the display screen, and the whole machine can meet the requirements of dropping from a height of 1.2 meters without being damaged.

In this embodiment, the functional module can also be configured on the combined modular structure, and is connected to the main bracket by means of the damping apparatus, thereby avoiding the influence of the vibration of the functional module itself on the accuracy of the functional module, and also avoiding the influence of the vibration of the functional module itself on other components, which is beneficial to ensure the normal operation of the whole machine.

Moreover, the main bracket of this embodiment has a shared accommodation chamber for accommodating any one of the battery and the functional module, and one of the auxiliary battery or the functional module can be selected when in use, so that the functional module and the auxiliary battery can be rapidly installed and replaced so as to meet different requirements of application with no need to be structurally designed with the maximized configuration. By arranging the thermal isolation compartment and the thermal isolation member, it is also possible to isolate the regions having different heat requirements and then dissipates heat for specific regions without adding a specific heat dissipation module, so that the heat dissipation can be more targeted to further improve the stability and reliability of the whole machine and effectively guarantee the service life of the whole machine.

The above contents are merely the preferred embodiments of the present disclosure, and are not intended to limit the present disclosure. Any modifications, equivalent substitutions or improvements made within the spirit and principles of the present disclosure are included within the scope of the present disclosure.

What is claimed is:

1. A medical device, comprising:
   a housing which includes a front side and a lateral side, and is provided with an inner cavity;
   a combined modular structure formed by connecting a board card and an interface panel to a main bracket;
   a first opening provided on the lateral side of the housing for an insertion of the combined modular structure; the first opening is connected with the inner cavity of the housing, and the interface panel covers the first opening when the combined modular structure is inserted into the inner cavity of the housing through the first opening;
   a first securing structure for securing the combined modular structure to the housing; and
   a screen assembly having a display function; the screen assembly is provided on the front side of the housing.

2. The medical device of claim 1, further comprising a second opening provided on the front side of the housing; the second opening is also connected with the inner cavity of the housing, and the screen assembly covers the second opening when the screen assembly is secured to the housing.

3. The medical device of claim 2, wherein the screen assembly comprises a screen body and a reinforcing member for reinforcing and supporting the screen body.

4. The medical device of claim 3, wherein a first elastic buffer member is provided between a lateral side of the reinforcing member and an inner wall of the second opening and/or between a lateral side of the screen body and an inner wall of the second opening.

5. The medical device of claim 3, wherein the reinforcing member comprises a supporting surface capable of being connected to a back side of the screen body, and a concave-convex structure capable of being mated with the housing, and a second elastic buffer member is provided in the concave-convex structure.

6. The medical device of claim 1, further comprising a second securing structure for securing the screen assembly to the housing; wherein the second securing structure comprises a transverse locking member for connecting the screen assembly to the housing, with a locking direction of the transverse locking member being perpendicular to a direction in which the screen assembly is inserted into the second opening, wherein the transverse locking member is inserted through the lateral side of the housing to securely engage the screen assembly when mounted within the second opening.

7. The medical device of claim 1, further comprising a second securing structure for securing the screen assembly to the housing;
   wherein the second securing structure comprises a second snap-fit part arranged on at least one side surface of the screen assembly, and a mating portion is correspondingly provided on the housing in a position enabling the mating portion to be mated with the second snap-fit part, and the screen assembly is fixedly connected to the housing via a transverse locking member passing through the second snap-fit part; or wherein the second securing structure comprises a first snap-fit part arranged on one side of the screen assembly and a second snap-fit part arranged on an opposite side of the screen assembly, the second securing structure further comprises a slot arranged on one side of the second opening and configured to be mated with the first snap-fit part, and a securing pin arranged on the opposite side of the second opening and mated with the second snap-fit part.

8. The medical device of claim 1, wherein the combined modular structure further comprises a functional module connected to the main bracket via a damping apparatus.

9. The medical device of claim 8, wherein the main bracket is provided with a hanging hole, the damping apparatus comprises a hanging part mated with the hanging hole, the main bracket is provided with a fixing strut, and the damping apparatus further comprises a hanging sleeve sheathed on the fixing strut.

10. The medical device of claim 9, wherein the damping apparatus comprises a second damping member arranged around or/and at the bottom of the functional module.

11. The medical device of claim 9, wherein a non-interference clearance is provided around the functional module, and the damping apparatus comprises a second damping member arranged at the bottom of the functional module.

12. The medical device of claim 9, wherein the damping apparatus is provided with a raised part making elastic contact with the main bracket.

13. The medical device of claim 9, the damping apparatus comprises an elastic tightening member for tightening opposite sides of the main bracket and the functional module towards each other.

14. The medical device of claim 1, wherein the main bracket is further fixedly provided with a thermal isolation compartment for accommodating a battery or a functional module.

15. The medical device of claim 14, wherein a surface of the housing is provided with at least one exposed window, and a part of the thermal isolation compartment extends to the at least one exposed window; or/and a thermal isolation member is provided in the housing, and the thermal isolation member is connected to the thermal isolation compartment.

16. The medical device of claim 15, wherein the thermal isolation compartment comprises a compartment body comprising a main body part capable of being configured for accommodating an internal object and an exposed part exposed from the at least one exposed window.

17. The medical device of claim 16, wherein the thermal isolation compartment further comprises a compartment cover connected to the compartment body, the connection between the compartment cover and the compartment body is provided with a sealing member; or/and at least one side of the compartment cover is provided with a reinforcing structure.

18. The medical device of claim 16, wherein the exposed part is provided with a venting groove, the exposed part is provided with an exposed plate, and the exposed plate is capped over the venting groove and partially exposes the venting groove.

19. The medical device of claim 1, wherein a plurality of circuit boards in the board card and the interface panel are respectively fixed on the respective surfaces of the main bracket to form a frame structure, a cavity is defined inside the frame structure.

20. The medical device of claim 19, wherein the medical device is connected to a medical module connection base, the medical module connection base comprises an input/output interface, the input/output interface comprises one or more of an AC input socket, a VGA socket, a multifunctional interface and a USB interface, and the board card comprises a connection interface corresponding to the input/output interface.

* * * * *